US008614369B2

(12) United States Patent
Osbourn et al.

(10) Patent No.: US 8,614,369 B2
(45) Date of Patent: Dec. 24, 2013

(54) ENZYMES INVOLVED IN TRITERPENE SYNTHESIS

(71) Applicant: Plant Bioscience Limited, Norwich (GB)

(72) Inventors: Anne Osbourn, Norwich (GB); Xiaoquan Qi, Norfolk (GB);

(73) Assignee: Plant Bioscience Limited (GB)

( * ) Notice: Subject to any disclaimer, the term of this patent is extended or adjusted under 35 U.S.C. 154(b) by 0 days.

(21) Appl. No.: 13/904,086

(22) Filed: May 29, 2013

(65) Prior Publication Data
US 2013/0247245 A1 Sep. 19, 2013

Related U.S. Application Data

(62) Division of application No. 12/664,891, filed as application No. PCT/US2007/014763 on Jun. 25, 2007, now Pat. No. 8,470,995.

(51) Int. Cl.
C12N 15/82 (2006.01)
C12N 15/87 (2006.01)

(52) U.S. Cl.
USPC .... 800/279; 800/320.3; 536/23.2; 435/320.1; 435/468

(58) Field of Classification Search
None
See application file for complete search history.

(56) References Cited

U.S. PATENT DOCUMENTS 7,186,884 B2    3/2007  Osbourn et al.
2006/0112448 A1 5/2006  Osbourn et al.

OTHER PUBLICATIONS

Kikuchi et al, 2003, Science, 301:376-379.*
Sasaki et al, 2002, UniprotKB/Swiss-Prot Accession No. Q6EPG8.*
Sasaki et al, 2003, UniprotKB/Swiss-Prot Accession No. Q69IV0.*
Wing et al 2000, GenBank Accession No. AC079179.5.*
Sasaki et al, 2003, GenBank Accession No. AP006173.*
K.R. Price et al., CRC Critical Review Food Science Nutrition. The chemistry and biological significance of saponins in foods and feedingstuffs, vol. 26, p. 27-133, 1987.
K. Papadopoulou et al., Proc. Natl. Acad. Sci., USA. Compromised disease resistance in saponin-deficient plants, vol. 96, p. 12923-12928, 1999.
J. A. Shi et al., Journal of Medicinal Food. Saponins from Edible Legumes: Chemistry, Processing, and Health benefits, vol. 7, p. 67-78, 2004.
E. H. Vis et al., Nutrition and Cancer. Possible mechanisms behind the differential effects of soy protein and casein feedings on colon cancer biomarkers in the rat, vol. 51, p. 37-44, 2005.
Oakenfull et al,, Nutrition Reports International. Prevention of dietary hypercholesterolaemia in the rat by soya bean and quillaja saponins, vol. 29, p. 1039-1046, 1984.
M. A. Berhow et al., Phytochemial Analysis. Analysis and quantitative determination of group B saponins in processed soybean products, vol. 13, p. 343-348, 2002.
J. Hu et al., Journal of Agricultural and Food Chemistry, Quantification of the group B soyasaponins by high-performance liquid chromatography, vol. 50, p. 2587-2594, 2002.
T. Kushiro et al., Eur. J. Biochem. Cloning of oxidosqualene cyclase that catalyzes the formation of the most popular triterpene among higher plants, vol. 256, p. 238-244, 1998.
K. Haralampidis et al., Proc. Natl. Acad, Sci. USA. A new class of oxidosqualene cyclases directs synthesis of antimicrobial phytoprotectants in monocots, vol. 98, p. 13431-13436, 2001.
X. Qi et al., Proc. Natl. Acad. Sci. USA. A different function for a member of an ancient and highly conserved cytochrome P450 family: From essential sterols to plant defense, vol. 103, p. 18848-18853, 2006.
P.M. Coutinho et al., Journal of Molecular Biology. An evolving hierarchical family classification for glycosyltransferases, vol. 328, p. 307-317, 2003.
T. Vogt et al., Trands Plant Science. Glycosyltansferases in plants natural product synthesis: characterization of a supergene family, vol. 5, p. 380-386, 2000.
E. K. Lim et al., The EMBO Journal. A class of plant glycosyltransferases involved in cellular homeostasis, vol. 23, p. 2015-2022, 2004.
B. Townsend et al., Phytochemistry Reviews. Saponin glycosylation in cereals, vol. 5, p. 109-114, 2006.
C. Milkowski et al., Phytochemistry. Serine carboxypeptidase-like acyltransferases, vol. 65, p. 517-524, 2003.
C. M. Fraser et al., Plant Physiology. An expression and bioinformatics analysis of the *Arabidopsis* serine carboxypeptidase-like gene family, vol. 138, p. 1136-1148, 2005.
A X. Li et al., PNAS. An acyltransferase catalyzing the formation of diacylglucose is a serine carboxypeptidase-like protein, vol. 97, p. 6902-6907, 2000.
L. G. Landry et al., Plant Physiology. *Arabidopsis* mutants lacking phenolic sunscreens exhibit enhanced ultraviolet-B injury and oxidative damage, Vol, 109, p. 1159-1166, 1995.
C. Lehfeldt et al., Plant Cell. Cloning of the SNG1 gene of *Arabidopsis* reveals a role for a serine carboxypeptidase-like protein as an acyltransferase in secondary metabolism, vol. 12, p. 1295-1306, 2000.
A. M. Shirley et al., Plant Journal. The SNG2 mutant of *Arabdopsis* is defective in the gene encoding the serine carboxypeptidase-like protein sinapoylglucose,choline sinapoyltransferase, vol. 28, p. 83-94, 2001.
C. Milkowski et al., The Plant Journal. Molecular regulation of sinapate ester metabolism in *Brassica napus*: expression of genes, properties of the encoded proteins and correlation of enzyme activities with metabolite accumulation, vol. 38, p. 80-92, 2004.

(Continued)

*Primary Examiner* — David H Kruse
*Assistant Examiner* — Jason Deveau Rosen

(57) ABSTRACT

This invention relates to isolated polynucleotides encoding enzymes consisting of a carboxypeptidase-like protein, a methyltransferase and a glucosyltransferase, involved in the biosynthesis of β-amyrin-derived triterpenes in plants and seeds. The invention also relates to the construction of recombinant DNA constructs comprising all or a portion of the isolated polynucleotides of the invention, in sense or antisense orientation, operably linked to at least one regulatory sequence.

19 Claims, 3 Drawing Sheets

(56) References Cited

OTHER PUBLICATIONS

A. Baumert et al., Phyochemistry. Formation of a complex pattern of sinapate esters in *Brassicana napus* seeds:catalyzed by enzymes of a serine carboxypeptidase-like acyltransferase family, vol. 66, p. 1334-1345, 2005.

K. Hostettmann et al., Saponins, Cambridge University Press. Occurrence and distribution, p. 18-105, 1995.

S. Frick et al., Phytochemistry. Combinatorial biochemistry in plants: the case of O-methyltransferases, vol. 56, p. 1-4. 2001.

D. R. Gang et al., Plant Cell. Characterization of Phenylpropene O-methyltransferases from sweet basil: facile change of substrate specificity and convergent evolution within a plant O-methyltransferase family, vol. 14, p. 505-519, 2002.

X. Qi et al., Proc. natl. Acad. Sci. USA. A gene cluster for secondary metabolism in oat: Implications for the evolution of metabolic diversity in plants, vol. 101, p. 8233-8238, 2004.

A. Christensen et al., Plant Molecular Biology A flavonoid O-methyltransferase is expressed in barley leaves in response to pathogen attack, vol. 36, p. 219-227, 1998.

A. E. Osbourn et al., Physiological and Molecular Plant Pathology. An oat species lacking avenacin is susceptible to infection by *Gaeumannomyces graminis* var. tritici, vol. 45, p. 457-467, 1994.

H. Jenner et al., Planta, Unravelling triterpene glycoside synthesis in plants: phytochemistry and functional genomics join forces, vol. 220, p. 503-506, 2005.

J. L. Peters et al., Trends in Plant Science, Forward genetics and map-based cloning approaches, vol. 8, No. 10, p. 484-491, 2003.

Sam T. Mugford et al., Serine Carboxypeptidase-Like Acyltransferase Is Required for Synthesis of Antimicrobial Compounds and Disease Resistance in Oats, Plant Cell, Aug. 2009, pp. 2473-2484, vol. 21.

Tetsuo Kushiro et al., Chimeric Triterpene Synthase. A Possible Model for Multifunctional Triterpene Synthase, J. Am. Chem. Soc., 1999, pp. 1208-1216, vol. 121.

\* cited by examiner

SEQUENCE LISTING

<160> NUMBER OF SEQ ID NOS: 9

<210> SEQ ID NO 1
<211> LENGTH: 1720
<212> TYPE: DNA
<213> ORGANISM: Avena strigosa

<400> SEQUENCE: 1

```
gcactagcta agctataccc gggcaaaaag gtcgtgacta gagatcgatc gagagatgga      60
gaagctgctc gtggtggtgc tgctgctagt gacgatctta gcattaggtg cagcggcgga     120
gagaactagg gtgacacacc tcaagggggtt cgatgggcct cttcccttct ccctggagac    180
cgggtacgtg gaggtggacg agacccatgg cgttgagctg ttctactact tcatcgagtc    240
ggagcgtaag ccggcagagg accccgtgat cctgtgggtc tccggcgggc ccggctgctc    300
gggcctgaac gccctcttct tcgagatcgg gcccctgaag ctggacatgg cgagctacgc    360
ggcgacggga ggaaaggggt tcccgggcct cctctacttc gaggacgcgt ggacgaaggc    420
gagcaacatg atattcctgg acgcgcccgt gggcgcgggg ttctcctacg cccgccaaac    480
ggaggggctc aacagcaccg tcaccgggct gggcaggcat gtgcgggtgt tcctccagaa    540
gtggatggcc cagcacccgg agctggcctc caacccgctc tacatcggcg gcgactcctt    600
ctccggctac accgtcaccg tctccgcgct ggaggtggcg aaccaccccg ccgccagcag    660
cgagctgaac ctcaaggggt acatggtggg caacgctcgc ggtgaagtga acaacgacaa    720
cgcctgcagg atcccctacc tgcacgggat ggggctcatc tccgacgagc tgtacgaggc    780
ggcgctgagc agctgtgtgg tggggacgga ttcgaagaac aagcagcagc aatctgctgc    840
acgatgctcc gaggcgcagc aggccatcag cgaagccacc acggacctca accctgcgca    900
catactggag ccggcgtgcg gagccgactt ctcacccaga gcgccttatc tgagcctcac    960
gacgccttct tcttcttctt cttcttcttc ttcttcttct tcttcttctt cttcttctta   1020
ttattatctg agcctgagta gtgtgaggag tcggacaccc accaaggaga tgctgctgga   1080
gtgccgtgtg tacgggtacg agctgtccta catgtgggct aacgacgccg aggtgaggga   1140
gaatctcggc gtccgggagg gcaccattgg tgacggcaac tgggcactgt gccccgaggt   1200
gcccaagctg cacctcacca acgacgtgcc caccaccgta ccctaccacc gccgcctcac   1260
gcagcgcggc taccgggcgc tggtgtacaa cggcgaccat gacttactca tgacccatat   1320
```

```
tgggacgcat gcatggatca ggtcactggg ataccccgtg gtggcgccct ggagggcctg   1380
gtactcaaac aacgaggtcg cgggcttcac cgtcgagtat tccaacaact taaccttcgc   1440
caccgtcaag ggcgccggcc acatggcgcc agagagccgc cctaagcagt gccttgacat   1500
ggtccgaaga tggatctcac ccgcaggaaa gctctaattc accaccacac cttgttgttt   1560
tggcacgcac gcacgtatgc atgcccccaa catcagaata gctagttgcc ttcatgcatg   1620
catgcatgca tccttcatct ttctatccat cacttttggt tgtaataata aatatgttgc   1680
gtgcaatgct taataaatat ttcatcttat tgggaaaaaa                         1720

<210> SEQ ID NO 2
<211> LENGTH: 493
<212> TYPE: PRT
<213> ORGANISM: Avena strigosa

<400> SEQUENCE: 2
```

| Met<br>1 | Glu | Lys | Leu | Leu<br>5 | Val | Val | Leu | Leu | Val<br>10 | Thr | Ile | Leu | Ala<br>15 |

Met Glu Lys Leu Leu Val Val Leu Leu Val Thr Ile Leu Ala
1               5                   10                  15

Leu Gly Ala Ala Ala Glu Arg Thr Arg Val Thr His Leu Lys Gly Phe
            20                  25                  30

Asp Gly Pro Leu Pro Phe Ser Leu Glu Thr Gly Tyr Val Glu Val Asp
        35                  40                  45

Glu Thr His Gly Val Glu Leu Phe Tyr Tyr Phe Ile Glu Ser Glu Arg
    50                  55                  60

Lys Pro Ala Glu Asp Pro Val Ile Leu Trp Val Ser Gly Pro Gly
65                  70                  75                  80

Cys Ser Gly Leu Asn Ala Leu Phe Phe Glu Ile Gly Pro Leu Lys Leu
                85                  90                  95

Asp Met Ala Ser Tyr Ala Ala Thr Gly Gly Lys Gly Phe Pro Gly Leu
            100                 105                 110

Leu Tyr Phe Glu Asp Ala Trp Thr Lys Ala Ser Asn Met Ile Phe Leu
        115                 120                 125

Asp Ala Pro Val Gly Ala Gly Phe Ser Tyr Ala Arg Gln Thr Glu Gly
    130                 135                 140

Leu Asn Ser Thr Val Thr Gly Leu Gly Arg His Val Arg Val Phe Leu
145                 150                 155                 160

Gln Lys Trp Met Ala Gln His Pro Glu Leu Ala Ser Asn Pro Leu Tyr
                165                 170                 175

Ile Gly Gly Asp Ser Phe Ser Gly Tyr Thr Val Thr Val Ser Ala Leu
            180                 185                 190

Glu Val Ala Asn His Pro Ala Ala Ser Ser Glu Leu Asn Leu Lys Gly
        195                 200                 205

Tyr Met Val Gly Asn Ala Arg Gly Glu Val Asn Asn Asp Asn Ala Cys
    210                 215                 220

Arg Ile Pro Tyr Leu His Gly Met Gly Leu Ile Ser Asp Glu Leu Tyr
225                 230                 235                 240

Glu Ala Ala Leu Ser Ser Cys Val Val Gly Thr Asp Ser Lys Asn Lys
                245                 250                 255

Gln Gln Gln Ser Ala Ala Arg Cys Ser Glu Ala Gln Gln Ala Ile Ser
            260                 265                 270

Glu Ala Thr Thr Asp Leu Asn Pro Ala His Ile Leu Glu Pro Ala Cys
        275                 280                 285

Gly Ala Asp Phe Ser Pro Arg Ala Pro Tyr Leu Ser Leu Thr Thr Pro
    290                 295                 300

```
Ser Ser Ser Ser Ser Ser Ser Ser Ser Ser Ser Ser Ser Ser Ser Ser
305                 310                 315                 320

Ser Tyr Tyr Tyr Leu Ser Leu Ser Ser Val Arg Ser Arg Thr Pro Thr
            325                 330                 335

Lys Glu Met Leu Leu Glu Cys Arg Val Tyr Gly Tyr Glu Leu Ser Tyr
            340                 345                 350

Met Trp Ala Asn Asp Ala Glu Val Arg Glu Asn Leu Gly Val Arg Glu
        355                 360                 365

Gly Thr Ile Gly Asp Gly Asn Trp Ala Leu Cys Pro Glu Val Pro Lys
    370                 375                 380

Leu His Leu Thr Asn Asp Val Pro Thr Thr Val Pro Tyr His Arg Arg
385                 390                 395                 400

Leu Thr Gln Arg Gly Tyr Arg Ala Leu Val Tyr Asn Gly Asp His Asp
            405                 410                 415

Leu Leu Met Thr His Ile Gly Thr His Ala Trp Ile Arg Ser Leu Gly
            420                 425                 430

Tyr Pro Val Val Ala Pro Trp Arg Ala Trp Tyr Ser Asn Asn Glu Val
        435                 440                 445

Ala Gly Phe Thr Val Glu Tyr Ser Asn Asn Leu Thr Phe Ala Thr Val
    450                 455                 460

Lys Gly Ala Gly His Met Ala Pro Glu Ser Arg Pro Lys Gln Cys Leu
465                 470                 475                 480

Asp Met Val Arg Arg Trp Ile Ser Pro Ala Gly Lys Leu
            485                 490

<210> SEQ ID NO 3
<211> LENGTH: 1198
<212> TYPE: DNA
<213> ORGANISM: Avena strigosa

<400> SEQUENCE: 3
tattctatca tcatggggca tgtccacact actagtgaaa acaaggcgat gatgagcacg      60
gaggagttcc tccaagctca gacggagctg tacaacctct ccttggctta tgtcaagtcc     120
gtggcactga gggccagcat agatctgcag atcccagagg ccatccaccg ccgtggtggt     180
tccgccacct tgtcggacat cgccgctgaa accgggaccc acgggacgaa ggtctcctac     240
ctcgggcggc tcatgcgcgt gctcgccatc tctggtgtct ctccatgca cagcgacgat      300 ggcgctgtgt actacaagct cacccacgta tcccgcctac tcgtgccagc cctatccccc     360
atggttcctg tgcttgtcga cccgctcgcc gcgaccgccc tcttcagcct agcagattgg     420
ttcaccgacg agcgggtgtc agagctcaca ctcttcgagg cggcgcacgg ctgcacgcgg     480
tcggagatga cagccaagaa gggcatgggc ggcatgttca acgccggcat ggtcgccgac     540
agccgcgtcc ttacggatat cctcctgagt gaacatggcg acatgtttga gggcgtggga     600
tccctggtgg acattggagg tggccatggt ggcgtcgctg aagctattgc caaggcgctg     660
cccgacatga aatgcaccgt gctagacctc ccacacgtgg tcaaagaggc agccaccggc     720
aatgtgcaat ttgtcgctgg ggatgcgttt cagtacatcc caccgccga cgcggttcta      780 ctcaagtggt ttttgcagtt gttcaacgac gaagatgcca tcaaggtgct agacggtgc      840 agggaagcca tccccgccaa aggaaaggtg ataatctttg atgttgtcgt ggggtcacac     900
tgcgaggacg ggcccaccag ggagacgcag cttttgtttg atatcttcat gatgcgcgtg     960
ggcgggcgtg agcgagaaga acaacagtgg aggaacatta tatttgaagc cggattcacg    1020
gactacaaga tctctgtagt attgggattt cgatctatca ttgaagtata cccgtgatag    1080
```

```
gtgcttcatt ttcatttgag aataatgcct tgctgctaca acactgttta caacactact    1140
tactacatgt ataccttctt ttttttttaca atgaatgcat ggcaagcttt ccaaaaaa     1198
```

<210> SEQ ID NO 4
<211> LENGTH: 354
<212> TYPE: PRT
<213> ORGANISM: Avena strigosa

<400> SEQUENCE: 4

```
Met Gly His Val His Thr Thr Ser Glu Asn Lys Ala Met Met Ser Thr
1               5                   10                  15

Glu Glu Phe Leu Gln Ala Gln Thr Glu Leu Tyr Asn Leu Ser Leu Ala
            20                  25                  30

Tyr Val Lys Ser Val Ala Leu Arg Ala Ser Ile Asp Leu Gln Ile Pro
        35                  40                  45

Glu Ala Ile His Arg Arg Gly Gly Ser Ala Thr Leu Ser Asp Ile Ala
    50                  55                  60

Ala Glu Thr Gly Thr His Gly Thr Lys Val Ser Tyr Leu Gly Arg Leu
65                  70                  75                  80

Met Arg Val Leu Ala Ile Ser Gly Val Phe Ser Met His Ser Asp Asp
                85                  90                  95

Gly Ala Val Tyr Tyr Lys Leu Thr His Val Ser Arg Leu Leu Val Pro
            100                 105                 110

Ala Leu Ser Pro Met Val Pro Val Leu Val Asp Pro Leu Ala Ala Thr
        115                 120                 125

Ala Leu Phe Ser Leu Ala Asp Trp Phe Thr Asp Glu Arg Val Ser Glu
    130                 135                 140

Leu Thr Leu Phe Glu Ala Ala His Gly Cys Thr Arg Ser Glu Met Thr
145                 150                 155                 160

Ala Lys Lys Gly Met Gly Gly Met Phe Asn Ala Gly Met Val Ala Asp
                165                 170                 175

Ser Arg Val Leu Thr Asp Ile Leu Leu Ser Glu His Gly Asp Met Phe
            180                 185                 190

Glu Gly Val Gly Ser Leu Val Asp Ile Gly Gly Gly His Gly Val
            195                 200                 205

Ala Glu Ala Ile Ala Lys Ala Leu Pro Asp Met Lys Cys Thr Val Leu
    210                 215                 220

Asp Leu Pro His Val Val Lys Glu Ala Ala Thr Gly Asn Val Gln Phe
225                 230                 235                 240

Val Ala Gly Asp Ala Phe Gln Tyr Ile Pro Pro Ala Asp Ala Val Leu
                245                 250                 255

Leu Lys Trp Phe Leu Gln Leu Phe Asn Asp Glu Asp Ala Ile Lys Val
            260                 265                 270

Leu Arg Arg Cys Arg Glu Ala Ile Pro Ala Lys Gly Lys Val Ile Ile
        275                 280                 285

Phe Asp Val Val Gly Ser His Cys Glu Asp Gly Pro Thr Arg Glu
    290                 295                 300

Thr Gln Leu Leu Phe Asp Ile Phe Met Met Arg Val Gly Gly Arg Glu
305                 310                 315                 320

Arg Glu Glu Gln Gln Trp Arg Asn Ile Ile Phe Glu Ala Gly Phe Thr
                325                 330                 335

Asp Tyr Lys Ile Ser Val Val Leu Gly Phe Arg Ser Ile Ile Glu Val
            340                 345                 350

Tyr Pro
```

<210> SEQ ID NO 5
<211> LENGTH: 1738
<212> TYPE: DNA
<213> ORGANISM: Avena strigosa

<400> SEQUENCE: 5

```
cgccagcaca aaagctccac gtactacgta tacgtcctct tactacctac taggattagc      60
tagcaatggg ggctgagtgg gagcacgtca gcgacatcca cgtcctcttg ctgccgtacc     120
cagtccaggg ccacatcaac cccatgcttc agttcggcaa acgccagcc cacatcggcg      180
gcgtcggcgt ccggtgcaca ctcgccatca cgccttacct cctgcgccag tgccaggacc     240
cgtgccccgg tgcggtccac ctcgtcgaga tctctgatgg cttcgacagc gctggcttcg     300
aagaggtcgg cgatgtcgcg gcctacctcg ccggcatgga gtccgccggg tcccgcaccc     360
tggacgagct gctccgctcc gaggcggaga agggccggcc gatacacgcg gtggtatatg     420
acgcgttcct gcagccatgg gtgccacgcg tggcgcggct acacggggcc gcctgcgtgt     480
ccttcttcac gcaggcggcc gccgtgaacg tggcctactc ccggcgggtt ggaaagatag     540
aggagggct ccccgctggg tttgaagccg aggatctgcc aacgttcctc accttgcccc      600
tgccgtacca agacatgctc ttgtctcagt tcgtgggcct tgacgccgtc gaccacgtcc     660
tcgtcaactc cttccacgag ctgcagccac aggaatctgc ctacatggag tcgacgtggg     720
gggccaagac agtaggcccc acggtgccgt cggcatacct ggacaagcgc atcaccgacg     780
atgtctccta tggcttccac ctctacaccc cgatgacggc cacgactaag gcctggctgg     840
acgcccagcc tccgcgctcc gtcacctacg tatccttcgg cagcatggcc acgcggggc      900
ccacggagat ggccgagatg gccgagggtc tacatagcag cggcaaggcc ttcctatggg     960
ttgttagggc atcggaggcc tcaaagatcc ctgacggatt ccaggaaagg gtgggtggga    1020
gaggactcgt ggtgacctgg gtggcgcagc tggaggttct agcacacggc gccatcgggt    1080
gcttcgtgac gcactgtgga tggaactcca cgatggaggc cctaggcgcc ggcgtaccga    1140
tggtggcggt accacagtgg tcggaccagc ccaccaacgc caagttcgtc gaggacgttt    1200
ggtgcgtcgg cgtccgcgcc cggcgggatc cggaagggt ggttaggagg gaggagttgg     1260
agaggtgcat tagggaggtg acggggacg acaagtatg atgcaatgcc ttagattgga      1320
aggagaaatc aaagagggcc atgtcccaag ggggtagctc agacatgaac atcacggaat    1380
ttcttcaagc actaagaagg tcaagaaaat catacgaggc gaaacctatc gaacctctgc    1440
tggtggggtt agatgcatga ataatcttgg gctacacggg tgtttgagct acacgtcaag    1500
atgggaatgg gcacgaaccg ggccccgttg ccccaggacc aatctcaggg gccacagatc    1560
gatccattct cataaaatac tatgccctg ctggcctatt gggtgcccag ggccgaccca     1620
attttctgct agaatacact ttttttaact ctgtatacgc acgataatat gacataaata    1680
gaggttacag aggaagtata aatccaatta acgatattaa aaaaaaaaaa aaaaaaa       1738
```

<210> SEQ ID NO 6
<211> LENGTH: 464
<212> TYPE: PRT
<213> ORGANISM: Avena strigosa

<400> SEQUENCE: 6

```
Met Gly Ala Glu Trp Glu His Val Ser Asp Ile His Val Leu Leu Leu
1               5                   10                  15

Pro Tyr Pro Val Gln Gly His Ile Asn Pro Met Leu Gln Phe Gly Lys
            20                  25                  30
```

-continued

Arg Leu Ala His Ile Gly Gly Val Gly Val Arg Cys Thr Leu Ala Ile
              35                  40                  45

Thr Pro Tyr Leu Leu Arg Gln Cys Gln Asp Pro Cys Pro Gly Ala Val
 50                  55                  60

His Leu Val Glu Ile Ser Asp Gly Phe Asp Ser Ala Gly Phe Glu Glu
 65                  70                  75                  80

Val Gly Asp Val Ala Ala Tyr Leu Ala Gly Met Glu Ser Ala Gly Ser
                 85                  90                  95

Arg Thr Leu Asp Glu Leu Leu Arg Ser Glu Ala Glu Lys Gly Arg Pro
            100                 105                 110

Ile His Ala Val Val Tyr Asp Ala Phe Leu Gln Pro Trp Val Pro Arg
        115                 120                 125

Val Ala Arg Leu His Gly Ala Ala Cys Val Ser Phe Phe Thr Gln Ala
130                 135                 140

Ala Ala Val Asn Val Ala Tyr Ser Arg Arg Val Gly Lys Ile Glu Glu
145                 150                 155                 160

Gly Leu Pro Ala Gly Phe Glu Ala Glu Asp Leu Pro Thr Phe Leu Thr
                165                 170                 175

Leu Pro Leu Pro Tyr Gln Asp Met Leu Leu Ser Gln Phe Val Gly Leu
            180                 185                 190

Asp Ala Val Asp His Val Leu Val Asn Ser Phe His Glu Leu Gln Pro
        195                 200                 205

Gln Glu Ser Ala Tyr Met Glu Ser Thr Trp Gly Ala Lys Thr Val Gly
210                 215                 220

Pro Thr Val Pro Ser Ala Tyr Leu Asp Lys Arg Ile Thr Asp Asp Val
225                 230                 235                 240

Ser Tyr Gly Phe His Leu Tyr Thr Pro Met Thr Ala Thr Thr Lys Ala
                245                 250                 255

Trp Leu Asp Ala Gln Pro Pro Arg Ser Val Thr Tyr Val Ser Phe Gly
            260                 265                 270

Ser Met Ala Thr Pro Gly Pro Thr Glu Met Ala Glu Met Ala Glu Gly
        275                 280                 285

Leu His Ser Ser Gly Lys Ala Phe Leu Trp Val Val Arg Ala Ser Glu
290                 295                 300

Ala Ser Lys Ile Pro Asp Gly Phe Gln Glu Arg Val Gly Gly Arg Gly
305                 310                 315                 320

Leu Val Val Thr Trp Val Ala Gln Leu Glu Val Leu Ala His Gly Ala
                325                 330                 335

Ile Gly Cys Phe Val Thr His Cys Gly Trp Asn Ser Thr Met Glu Ala
            340                 345                 350

Leu Gly Ala Gly Val Pro Met Val Ala Val Pro Gln Trp Ser Asp Gln
        355                 360                 365

Pro Thr Asn Ala Lys Phe Val Glu Asp Val Trp Cys Val Gly Val Arg
370                 375                 380

Ala Arg Arg Asp Pro Glu Gly Val Val Arg Arg Glu Glu Leu Glu Arg
385                 390                 395                 400

Cys Ile Arg Glu Val Thr Gly Asp Asp Lys Tyr Ala Cys Asn Ala Leu
                405                 410                 415

Asp Trp Lys Glu Lys Ser Lys Arg Ala Met Ser Gln Gly Gly Ser Ser
            420                 425                 430

Asp Met Asn Ile Thr Glu Phe Leu Gln Ala Leu Arg Arg Ser Arg Lys
        435                 440                 445

Ser Tyr Glu Ala Lys Pro Ile Glu Pro Leu Leu Val Gly Leu Asp Ala
450                 455                 460

```
<210> SEQ ID NO 7
<211> LENGTH: 6000
<212> TYPE: DNA
<213> ORGANISM: Avena strigosa

<400> SEQUENCE: 7
tttcgtcgca ccaaaaagcc attttctatt tttcgagcat aaaaaacgga cggttttgtg      60
aagcaaccac caaatggcta attcaaaata ctaccaccac attttacaaa aatactatac     120
caccttatat ggacaatgtc ccaacagggg gatccgaaac ctttccgtcc acctttggtg     180
aaaaagacaa attcctgccg aatcggtagg aagtgggtca gatatgaact acagggacat     240
gatccgatgc tcatgttttt ttacaaaaat cattttaggg ttcacaatat gctattttat     300
caaagatcta atgaaagttt agcgaggctc tgccccgagc taagaatctt tatgtccgcc     360
gttcgacaaa gtttgacgat ggtttaaaac gggcataaaa aattcaaaaa cgatcgaaac     420
aatgcgaaag gttcgcgtgg tgtcatatta tgtgacatag ttataagaaa aaatagcaaa     480
cttgatatat ttattatgtc tcaaaaaacc ttcacaaaat gacatatctg attcgaggtt     540
tcttggcttt cgggtgaaat gaccaatgtt atggctagaa tcaaggcata gtttgtgata     600
atgtgcccaa attatgcata cacatgcatc atgggatggc gaacaatgtt gcaggaggaa     660 gttttttcttt tcgtcgcact aaaaagccat tttctatttt ccgagtataa aaaacggacg     720
gttttgtgaa gcaaccacca aatggctaat tcaaaatact accaccacat tttataaaaa     780
tactatacca ccttatatgg acaatgtccc aacaggggga tctgaaacct ttccgttcac     840
ctttggtgaa aaagacaaat tcctaccgaa tcggtaggaa gtgggtcaga tatgaactac     900
aggtacatga tccgatgctc atgttttttt acaaaaatca ttttaggtt cacaatatgc     960 tattgtatca aagatctaat gaaagtttag cgaggctcgg ccccgagcta agaatcttta    1020
tgtccgccgt tcgacaaagt gtgacgatag tttaaaacgg gcataaaaaa ttcaaaaacg    1080
atcgaaacaa tacgaaagct tcacgtggtg tcatattatg tgacatagtt ataagtaaaa    1140
atagcaaact tgatatattg attatgtctc aaaaaacctt cacaaaatga cctatctcat    1200
tcgaggtttc ttggctttcg ggtcaaatga ccaatgttat ggctagaatc gatgcatagt    1260
ttgtgataat gtgcccatat tatgcataca aatgtatcat gggatggcga acaatgttac    1320
aggaggaagt tttccttttc gtcgcaccaa aaagccattt tctatttttc gagcataaaa    1380
aacggacggt tttgtgaagc aaccaccaaa tggctaatta aaaatactac caccacattt    1440
tacaaaaata ctataccacc ttatatggac aatgtcccaa cagggggatc cgaaaccttt    1500
ccgtccacct ttggtgaaaa agataaattc ctgccgaatc ggtaggaagt gggtcagata    1560
tgaactacag gtacatgatt caatactcat gttttttaaca aaaatcattt ttaggtttac    1620
aatatgctat tttatcaaag atctaatgaa attttagcga ggctctgccc cgagctaaga    1680
atctttacgt ccgccgttcg acaaagtttg acgatagttt aaaacgggca taaaaaaatc    1740
aaaaacgatc gaaacaatgc gaaaccttcg tgtggtgtca tattatgtga catatttata    1800
aggaaaaata gcaaacttga tatattgatt atgtctcaaa aatccttca caaaatgacc    1860 tatctcattt taggtgtctt ggctttcggg tcaaatgacc aatgttatgg ctagaatcaa    1920
ggcatagttt gtgataatgt gcccatatta tgcatacaca tgcatcatgg gatggcgaac    1980
aatgttgcag gaggaagttt tccttttcgt cgcaccaaaa agctattttc tatttttcga    2040
gcataaaaaa cggacggttt tgtgaagcaa ccaccaaatg gctaattcaa aatactacca    2100
ccacatttta caaaaatac tataccacct tatatggaca atgtcccaac aggggatccg    2160
aaacctttcc gtccaccttt ggtgaaaaag acaaattccc gccgaatcgg taggaagtgg    2220
```

```
gtcagatatg aactacaggt acatgatccg atgctcacgt ttttttacaa aaattatttt   2280
taggttcaca atatgctatt ttatcaaaga tccaatgcaa cttttccttt tcatcgcacc   2340
aaaaaggcat ttttcattat ccgagcgcaa aaagggatt ttctaaagca accaccaaat    2400
agctaattcg aaaacggagg gtttgtgatt atttgatatg gatatcatat ttggattcct   2460
ctcattttta tgatcaattt aaacatatta tttgttgaat ttcgatttac agatttaaag   2520
atattaatta ttctatatta aatagaaaaa tacaaaaaaa ataaaattat tatattttta   2580
tttgaattca ataatatttt tacttattca ttaatattta cttaaataat tgtttgtaat   2640
tttaaaaaat acaaacatgt gacatgatga tataagagtt aataagattg atatcatagt   2700
attgacacca atgtatgaat taatttgcgg aaacggattc tgaaggaacg agaaagttaa   2760
gcgtgctgaa gctggagtag tataggatgg gcgaagttca gttcaaaaga ccgcagcgga   2820
gtggagcagc cgcgacacga agttccttac cttagctgga tctcgctggt gccacctaaa   2880
cgacctcttg ggaagtttga ctaagactgg aatttaatca aatagtaagt ataattagtg   2940
ttaaacatgt tcaaagtagg agattaacaa gtgaaacaat tcaaagaata aattttttta   3000
gaaaaataaa taaaaaaatt attattattc aaaaataaaa aaatcaaaaa agaaatattt   3060
ttgcaaccgg tcgacgccga cggcaaagcc ttcgacgtag catacgccga cgccgatggc   3120
ttgactgtgc tccgccgagg gagatctttg cccgaggagc cctcggcgta ccatacgccg   3180
agggcatttt ggcctacgcc gacggccttt ttccctcggc gtagcgcgcg cgtcccatag   3240
tgaaattaac tagatatatc tctcttctcg agtgagcttg agtactagtg gtacgtgctt   3300
tttatttatc atctcgtggc agaaatagg tttaaaagga gccacgatta ttgatggacg    3360
cactagctaa gctatacccg ggcaaaaagg tcgtgactag agatcgatcg agagatggag   3420
aagctgctcg tggtggtgct gctgctagtg acgatcttag cattaggtgc agcggcggag   3480
agaactaggg tgacacacct caaggggttc gatgggcctc ttcccttctc cctggagacc   3540
gggtacgtgg aagtggacga gacccatggc gttgagctgt tctactactt catcgagtcg   3600
gagcgtaagc cggcagagga ccccgtgatc ctgtgggtct ccggcgggcc cggctgctcg   3660
ggcctgaacg ccctcttctt cgagatcggg cccctgaagc tggacatggc gagctacgcg   3720
gcgacgggag gaaaggggtt cccgggcctc ctctacttcg aggacgcgtg gacgaaggcg   3780
agcaacatga tattcctgga cgcgcccgtg ggcgcggggt tctcctacgc ccgccaaacg   3840
gaggggctca acagcaccgt caccgggctg gcaggcatg tgcgggtgtt cctccagaag    3900
tggatggccc agcacccgga gctggcctcc aacccgctct acatcggcgg cgactccttc   3960
tccggctaca ccgtcaccgt ctccgcgctg gaggtggcga accaccccgc cgccagcagc   4020
gagctgaacc tcaaggggta catggtgggc aacgctcgcg gtgaagtgaa caacgacaac   4080
gcctgcagga tcccctacct gcacgggatg gggctcatct ccgacgagct gtacgaggcg   4140
gcgctgagca gctgtgtggt ggggacggat tcgaagaaca agcagcagca atctgctgca   4200
cgatgctccg aggcgcagca ggccatcagc gaagccacca cggacctcaa ccctgcgcac   4260
atactggagc cggcgtgcgg agccgacttc tcacccagag cgccttatct gagcctcacg   4320
acgccttctt cttcttcttc ttcttcttct tcttcttctt cttcttcttc ttcttcttat   4380
tattatctga gcctgagtag tgtgaggagt cggacaccca ccaaggagat gctgctggag   4440
tgccgtgtgt acgggtacga gctgtcctac atgtgggcta acgacgccga ggtgagggag   4500
aatctcggcg tccggggggg caccattggt gacggcaact gggcactgtg ccccgaggtg   4560
cccaagctgc acctcaccaa cgacgtgccc accaccgtac cctaccaccg ccgcctcacg   4620
```

```
cagcgcggct accgggcgct ggtgtacaac ggcgaccatg acttactcat gacccatatt      4680
gggacgcatg catggatcag gtcactggga taccccgtgg tggcgccctg agggcctgg       4740 tactcaaaca acgaggtcgc gggcttcacc gtcgagtatt ccaacaactt aaccttcgcc      4800
accgtcaagg gcgccggcca catggcgcca gagagccgcc ctaagcagtg ccttgacatg      4860
gtccgaagat ggatctcacc cgcaggaaag ctctaattca ccaccacacc ttgttgtttt      4920
ggcacgcacg cacgtatgca tgcccccaac atcagaatag ctagttgcct tcatgcatgc      4980
atgcatgcat ccttcatctt tctatccatc acttttggtt gtaataataa atatgttgcg      5040
tgcaatgctt aataaatatt tcatcttatt gggaccttga tttcttgttt ggatctgacc      5100
cggcctccaa tcattttat ggaagcctat atatatatat atatatctct ctctcatata       5160
tatatatata tgagagagag atatttcata aacaaaacat ttatatgaaa tcatatttgc      5220
actacaggaa tgagaagcta cgccgacggc caaacgtcgg ggccgtcggc gtagtcatcg      5280
tctaggccag ctccgctagc cgtcggcgta gaattgtcgt tggcatatcc tatgctacgc      5340
cgacggctgc cctcggcgca gctatttttt attttatctc attaaacttt gaaaaatcat      5400
aactaaatca ttctaattcg aaaaaataca aataatatat caaaatttgc agaaaaataa      5460
tacctatcta tctacactca aatattacac atatgtaaat aaaaattaaa taaaacataa      5520
aacattatat atagtttaaa acgagcataa aaaaattcaa aaataatcga aacaatgcga      5580
aaccttcgtg tggtgttata ttatgtgaca ttgttagaag gaaaaatatc aaacttggta      5640
tattgattat gtcttaaaga aaccttcaca aaatgatcta tctcattcga ggtttcttgg      5700 cttttcgggtc aaatgaccaa tgttatggct agaatcaagg catagtttgt gataaatatgc     5760 ccatattgtg catacatgtg taccatagga tggtgaacaa tattgcagga ggaatctttc      5820 cttttttgtcg caccaaaaag gcattttcca ttttccgagt ataaaaaca gacggttaaa      5880 caactaccaa atggctaatt caaaatacta ccaccacatt ttaaaaaaat aatagagcac      5940
cttatatgga caatgtccca acaggggat ccgaaacctt tccgtccacc tttggtgaaa       6000
```

<210> SEQ ID NO 8
<211> LENGTH: 6000
<212> TYPE: DNA
<213> ORGANISM: Avena strigosa

<400> SEQUENCE: 8

```
ctaatgttgt ttgtccttct actattactc tcccattctt gccatactaa aagcaaaata       60
aaacacttat gtttccaacg gggaattttt tgttgtatat tatagccaag agctggagta      120
tgcccgcgat ttgggttatt agattgtacc actcagggat tacttgtttg aggagatgat      180
tggtcctttc aaaatatttg tgcgagatct ctttgccagc agacaagaag ctaaaaataa      240
tggtgacgat gctatggcat atgtttacaa gattttcatg aactcactat acgggagatt      300
gggtattaat tcggaaagta ctataatgga ggtatgcaaa aaaggaatga tatgactatt      360
tgatacagaa ctctaatttc atctcaggag atatgctaag cgatcattac tatatactca      420
gttagaatag caaaacaaga catgttgaca actcatctga ctagaatctt cctacaaaca      480
caaatgttca catctgaccg agcatctggt gccgcacttg catttggtg cattcttctt       540 cttttttcttg gtcctaagtt ccgtcatagc taaataactt atctaattat aacgtattaa     600
ccgttaatgt accttttttt aatcaaatct caggacatgg tctaatcatg agggtagtat      660
tttatcatgt gttggatcc caagttttta caattcttgt tttgttccgg ggtcgaccat      720
aaagccataa tgtctcaaaa tgaagagact atagaatcag ctgcctcact gtgcaacaag      780
```

```
acggatacct gaccaactct tgcctggttg gagatctcaa tgcaatgtcg gtggtcaatt      840
aagatcatca gttcattaat ggaattgtag atctcgatgt atatagtatg attcttacaa      900
cttgatattt gttttgcaa actagtcata ggggaagtaa ttttactac acatgcttag         960 tctatgttac aacctaaact cttactattt attaacttga cttattctat cttaggccgt     1020
gtcaatggta cgagcagcta tttatcacaa tcatctctct catcacttaa cggcttgcca     1080
tgtcatcagt atgcccagtt aacactgcat atagctcttt gttactacca atattactct     1140
cactatgaat agtcgcgttg gcacctaatc tgggttcgtt tgttatctaa tctccatgct     1200
tggtgcttga tcggacgctc taagacacat gcgttgggta aaatagtact agatggtata     1260
tattaggagg ccttgcggaa ttcatggagc attttatgt gttgtctgct atgagggtct      1320
gacatatgca tacactgaca ggtaacagac aattactggc ctttattttc cgcgatcctc     1380
gttggtagaa ccctaagcat atatcgtagg tcaatcaaga caagatatga tgaactcatt     1440
aaatggagtt tgagatctca acgtaaggtg gtcaaacaag aactgatcta cagatcttga     1500
tgtatgattc ttgcaaattt ttgtaaattt attccatcaa gctactagat ctacaattcc     1560
cgctcacggt gaagcttcta tctctgtacc atctttccat cgaatgtaag acctgggaaa     1620
aatgtacaca ccaatattag ccttattagt ctttaggtac gcttcgtgat agtctctgag     1680
taccccgccg ccgaattcgc cagtatctcc ctacatcttg atccctggaa aggggtggtc     1740
cttagtccgt ttcgattcgt gccatgtcct gattttggtt caatgtttga ttttaacat      1800 gaggaaaact tataagcccg tacgaatgaa gtactattat taattatcct tactcgctaa     1860
cagatcccgg gatccgccga actagttatc gagtcccgac agtgaggcgg agagacgtag     1920
gtgccagtga aaactgagcc attggtgggt gatagcggcg ttaccacatc gttacattga     1980
cgaaggaatc atcgtgcacc cagtgtcgac ctaaatcgtg ctacttcaac gtaaaccata     2040
agatcttcgg atcgggcgat ggcggcgcca cgacgttgtg ttctctctta ggaggatcgc     2100
ttctggagca gcgctagatg gaagaggcag gagagacgga gtggctagca cgcaggatgg     2160
tggttctact tggcaccaca gtgatgtcgg tggcaggtat ggcgagagtc tacgcatcga     2220
tctacatgct aaagatggtt tggccaaaga tagtgaaggc ggcgacatcc ggagtgtgtg     2280
cgttgttctg tggataggct gtgcggatct agggctcctt ttgtatgagt tcaagccgcc     2340
acgcccaggc gctccttctt ctcttgcgag tcactgagag agagcgagag attgtggcac     2400
ggggtcgaaa gcagcagcca gctgtttgct agatcttgtc ggggaactgg cgatacagtt     2460 atcgttttc tcggtgattt gttttggga tctattttta taatctttct aatagatgtt      2520
gccaaacact ttggttcgaa gaataaagcc ggtcatagtg ggagtaattt agctatacca     2580
aataagcaaa ctggtgacat gacatgataa ttaataaaga aagagagaaa gatagtaact     2640
tagctattta gttatcataa caccacacat atcaataata tatgagtcta taatctaatt     2700
aaatagtctt taaatgaaac cacacatatg ttactaccca ctataaagat agtaacatga     2760
actagtaaca tatacatgtt actagtctaa gttacttagc actatgacca acctaaaggt     2820
tgtgtgcata gctacatgca aggctttgct cgcatttcgg aaaaggatt aattatcctt      2880 actactggca acttattagt ttattaggct tgccggtgta tctatgtcct taattcgacc     2940
aatgtaaaat aaatcatata atacaaaaat cataccatta aaaataaca tctaaagttt      3000 ataataatat gttttagtaa tatatacttc agttggtccc aacaagatac acgtccaagg     3060
ctaataaaat aacaaggaga gagctagtaa tatacacacg ttgaagccta ataatttagt     3120
gctatcctca gtgaggtgtt tgctactcta gctactagtg gagtaggcta taagagggcg     3180
```

-continued

| | | | | | |
|---|---|---|---|---|---|
| atgagggata | gcaaaggttt | ttgtgtcact | caccacacaa | gacaagatat | tctatcatca | 3240 |
| tgggcatgt | ccacactact | agtgaaaaca | aggcgatgat | gagcacggag | gagttcctcc | 3300 |
| aagctcagac | ggagctgtac | aacctctcct | tggcttatgt | caagtccgtg | gcactgaggg | 3360 |
| ccagcataga | tctgcagatc | ccagaggcca | tccaccgccg | tggtggttcc | gccaccttgt | 3420 |
| cggacatcgc | cgctgaaacc | gggacccacg | ggacgaaggt | ctcctacctc | gggcggctca | 3480 |
| tgcgcgtgct | cgccatctct | ggtgtcttct | ccatgcacag | cgacgatggc | gctgtgtact | 3540 |
| acaagctcac | ccacgtatcc | cgcctactcg | tgccagccct | atccccatg | gttcctgtgc | 3600 |
| ttgtcgaccc | gctcgccgcg | accgccctct | cagcctagc | agattggttc | accgacgagc | 3660 |
| gggtgtcaga | gctcacactc | ttcgaggcgg | cgcacggctg | cacgcggtcg | gagatgacag | 3720 |
| ccaagaaggg | catgggcggc | atgttcaacg | ccggcatggt | cgccgacagc | cgcgtccttta | 3780 |
| cggatatcct | cctgagtgaa | catggcgaca | tgtttgaggg | cgtgggatcc | ctggtggaca | 3840 |
| ttggaggtgg | ccatggtggc | gtcgctgaag | ctattgccaa | ggcgctgccc | gacatgaaat | 3900 |
| gcaccgtgct | agacctccca | cacgtggtca | aagaggcagc | caccggcaat | gtgcaatttg | 3960 |
| tcgctgggga | tgcgtttcag | tacatcccac | ccgccgacgc | ggttctactc | aaggtactat | 4020 |
| acatttgttc | gttttttctc | cttttgaca | aaagcatatg | taaatttttc | tctctctcat | 4080 |
| tttttctagc | tacccaatgt | aataaaacctt | ttttttagca | aaggactgac | gtataaacca | 4140 |
| atgaactact | acgtacagtg | gttttttgcag | ttgttcaacg | acgaagatgc | catcaaggtg | 4200 |
| cttagacggt | gcagggaagc | catccccgcc | aaaggaaagg | tgataatctt | tgatgttgtc | 4260 |
| gtggggtcac | actgcgagga | cgggcccacc | agggagacgc | agcttttgtt | tgatatcttc | 4320 |
| atgatgcgcg | tgggcgggcg | tgagcgagaa | gaacaacagt | ggaggaacat | tatatttgaa | 4380 |
| gccggattca | cggactacaa | gatctctgta | gtattgggat | ttcgatctat | cattgaagta | 4440 |
| tacccgtgat | aggtgcttca | ttttcatttg | agaataatgc | cttgctgcta | caacactgtt | 4500 |
| tacaacacta | cttactacat | gtataccttc | ttttttttta | caatgaatgc | atggcaagct | 4560 |
| ttccaacgat | tatacttatg | tccttttttg | tcaatatggc | aataatttcg | gaaacagtct | 4620 |
| ggtcttgaag | caaatatggc | acaatgtgca | cgagttgtta | gcataaaaca | accatatatt | 4680 |
| gatttaaatt | tctgctattg | tataaactta | cgatttgcgg | ataaaaatct | accatatttt | 4740 |
| gttaaggaga | aaaacaataa | tctcgagttg | aacacgaatt | gacgctattt | ctgacagaag | 4800 |
| agagacccac | atgccgggtc | ctatttgctc | atgtggactg | ggtcccattt | gtcatcccac | 4860 |
| attaaagagt | caaatatac | cataaataaa | agaaaaatcc | cctcactatt | ctctttcctc | 4920 |
| ctctctctct | ctctcacaca | cacaccacgg | tggcaggcca | ctccagcgac | catgcggggt | 4980 |
| ggcgaggac | gatgcacgcg | aggccacatg | cagcttgtag | gtcgggaaga | cgtcggcctg | 5040 |
| atcatagtgg | agaggtcgat | gcaccggacg | atgctcgcgt | tcagctccag | cgccactgtc | 5100 |
| acgccccgag | ctcacatacg | agcaccactg | tcaagcctcc | tggacatcct | cttagccgtc | 5160 |
| ctcctgcacc | cccttgcacg | ccccccgtccg | cacgtgtcac | gatccttggc | cgcgccatcc | 5220 |
| acgcactggc | gccactccag | ggcgcccctt | gtcacgcacc | tccttggtca | tggccaactt | 5280 |
| ggtcactggc | tttgggcgca | cttggagaga | gtggcacggg | gaggggataa | gggagtggca | 5340 |
| gcggatctcg | gcctcaagac | ggtggacaag | atagaggcac | tcggccacga | gcaaggtcat | 5400 |
| cggagaggac | tgctcccacc | agcggcggtg | gtaattgggt | gaggaagaat | gatgggtatt | 5460 |
| ttttataatt | gtaatttttt | atttaactga | catgtggacc | ccactccaag | tcagcaaatt | 5520 |
| ttgccaccctt | atccaagaaa | aacgggtact | cagatttcat | gtgaattcac | atttaattcg | 5580 |

-continued

| | |
|---|---|
| agtttagtgt tttttttgcg acctcccgag gaaaatgtgg tctactgcta tggatcgagc | 5640 |
| ggaggtctct cctcctccca ggctagagag gatgccctct tgggcaaaga agttgatgaa | 5700 |
| gaagatcaag aaatccttt gcttcatgca agaccacggg taccaagcat atgttgaccg | 5760 |
| gaggcatagt gccaagagag agaaggccaa catgaggaaa ctctgatatt aatgtctctc | 5820 |
| ctgagtccag ctctgtcacc gcgtccatgg gtgaatatga actgcaggtg gtctgaaaat | 5880 |
| gatgaagaga atgatgatga cgtcaccggt ccccctccac acgcttggga tcacgccacc | 5940 |
| tggaactccg atccctctcg tacttatgtt ggtggttggg gcatgtagat tggcctgtct | 6000 |

<210> SEQ ID NO 9
<211> LENGTH: 6000
<212> TYPE: DNA
<213> ORGANISM: Avena strigosa

<400> SEQUENCE: 9

| | |
|---|---|
| gaggaagggg ggtgggtggg ggtggagggg gaccgaagca aaagtgtgtg taaatttatt | 60 |
| cgatcaagct agcttactgg ggctgcactt ctggctgacg atgaagatcc tattttgaa | 120 |
| tcatctttcc atcaaatgta aaacttgata aaaatgtaca caccaatatt agtcttatta | 180 |
| ctccctctgt ctcaaattac tctgcattct aggtttggtc aaagtcagac ttattaaaac | 240 |
| ttatccaagc atattctaca aaataccaac atttataaaa tttatataca atataaaagt | 300 |
| atgttttatg atgagtctaa ttatatttat ttcatatttt agatgttgat attttttctg | 360 |
| atatacatag tcaatgttta aaagtttggg ctttaattaa acccaaaata cagagtaatg | 420 |
| agacagaggg agtagtattt aggtacgtct aatggatgtt gtcgaggaag gccaccggta | 480 |
| aaattatata tgatcttacc tacgatattg catgggtgc cataaaggtt gctagacctc | 540 |
| aatgcagacc acttgcaagt agggctggac tataacaagc tactcgactc gttaaggctc | 600 |
| ggtccgtata gctcgtgatc gttgattgtt cagataatta agaatatcaa gctaaaaatc | 660 |
| attgtttgac cctgttcgtt gcgtgctcac gagctctcac aagcagcgta ttaagattgt | 720 |
| ttagaaaata gtggctaact agctaagtgg tacatacatg atacatgtac gtggtaggga | 780 |
| ataattgtta ggaagtgaag cctagctcaa ctagttggga gagtgaatgt acaaattgaa | 840 |
| cacctggatt caaatcctca cggatgtgaa tttagattcc tatttatact tgaggaccaa | 900 |
| actatcctgg tactcatgaa gtatatcttg aggatcaggt ttggtactaa accaagttta | 960 |
| aaaatcctga tactcatgct taatggttgt gtccatcctt aattggtgca gagtccgggg | 1020 |
| aagtgaaatt ttccctccat ttttctttat cgaaaaaatg tacatggtag gatgggttgc | 1080 |
| cgctgctgaa gtgaagatga tgagatgagg agttcacaag aaaatcaatg agacaattga | 1140 |
| ggaggattga ggaatcgatg catcaattcc tgtactttat tttcggcgat cctcgttggt | 1200 |
| ataacctaag catatatata gcaagtcaaa caagacaaga tatgatgaac tcattaatgg | 1260 |
| cggttgagat ctcaatgtaa ggtggtcaaa caagacgaga atgatctat agatcttgat | 1320 |
| gtatgattgt tacaagtctg tgtaaattta ttagatcaag ctagctttgt ggggctgcaa | 1380 |
| ttctggctca cgatgaagct tgtatttctg aatcatcttt ccatcaaatg taaaacctgg | 1440 |
| aaaaaatgta cacaccaata ttagtcttat tagtatttag gtacatctaa cgtatgttgt | 1500 |
| ccagggaagc caccggtaaa attacatatg atcttacttg cgatatgggc atgggtgcca | 1560 |
| taaaggttgc tagacctcca ggcaggccac ttgcaagtag ggctggacta acaagctacc | 1620 |
| ccactcgtta aggctcggcc tgtttagctc gtgatcgtta aggcttagat tgttcagaca | 1680 |
| attaagaata acaagctaaa tttttcaaaa aaataataac aagctaaaaa tcattgtttg | 1740 |

```
accatgttcg ttgcgtgctc gcgagcgctc acaagcagca cattaagatc gttaagaaaa    1800
aatattggct aagtggtaca tacatgatac atggatgtac aaatctaaca cctcagttca    1860
aatcctcacg gatgtgaatt taggttccaa tttatatttg aggatcagac tattctagta    1920
ctcatgcaat atatcctggg accaggtttg gtacttaacc aactcatact taatggcagt    1980
gtcctctctc cattttttctt tatcgaaaat caaggagaca attgaggagg attgaggaat    2040
ctcgatgcat caaagggatg ttatattggt atttactagt ccccagtaag tactacccaa    2100
gtaggcatcg ctttgataat tgagcagctt ctcggggctt cggaccctttt gaccgttcaa    2160
aaaaaaaggt aggcatcgcc ccggtatgat cctgggagcc cggggaactt ggcctgggcc    2220
tttgggctgt tttcgtcatt tcaagtttgt ctgttagata ttctatgaat tagggagtgt    2280
aatgagatac tctcaagcct ctcgcttgtg tagctcgtgt taacgatagc gagctaaatt    2340
cgttgtttgg ctccgtttat ttactacacc gagcagagct aaacgagtct atcagacgat    2400
tgttgaattg gctcgctgag cttgaagctt tatatccatc cctatacccc cgcaaggcat    2460
cacatgtgaa gtcgtggatc ttatcatgat gactaccatg gatgtcatgc ctaaatggtc    2520
ttagtgtatt aactgcaaat taagacatca acttcttggg tcgattcgaa agaagaacct    2580
gggaaataat ataatgtgaa caactagcta gttaaccttt tgcggatttt tttagatgga    2640
ccgggtctga gctagcagca catcattgga tccaagctaa catatactac ctctcatttg    2700
ttttccataa tattagacgt tttggtagcc tactaatact aaaacaccgt atatttcgga    2760
ctggtgggag aaacaaataa gtgaaacagt gtagcagttc atggaccgat atgggagcga    2820
ggaagaaaaa aaacggcagt tagcaacgtt attgatccaa tggatcgccc acagcagatt    2880
cacacagtag tataaatgca acgttattga cgcaatatca tctccacaag ctactagccg    2940
cgccagcaca aaagctccac gtactacgta tacgtcctct tactacctac taggattagc    3000
tagcaatggg ggctgagtgg gagcacgtca gcgacatcca cgtcctcttg ctgccgtacc    3060
cagtccaggg ccacatcaac cccatgcttc agttcggcaa acgcctagcc cacatcggcg    3120
gcgtcggcgt ccggtgcaca ctcgccatca cgccttacct cctgcgccag tgccaggacc    3180
cgtgccccgg tgcggtccac ctcgtcgaga tctctgatgg cttcgacagc gctggcttcg    3240
aagaggtcgg cgatgtcgcg gcctacctcg ccggcatgga gtccgccggg tcccgcaccc    3300
tggacgagct gctccgctcc gaggcggaga agggccggcc gatacacgcg gtggtatatg    3360
acgcgttcct gcagccatgg gtgccacgcg tggcgcggct acacggggcc gcctgcgtgt    3420
ccttcttcac gcaggcggcc gccgtgaacg tggcctactc ccggcgggtt ggaaagatag    3480
aggaggggct ccccgctggg tttgaagccg aggatctgcc aacgttcctc accttgcccc    3540
tgccgtacca agacatgctc ttgtctcagt tcgtgggcct tgacgccgtc gaccacgtcc    3600
tcgtcaactc cttccacgag ctgcagccac aggtacgcta tagtatatgt agcccatata    3660
tatatcatcg atcagtcgtg tcatgtcatg tcatttatat atatacttgt atagtcgacg    3720
tttacttatt acatcctgaa atgaaatgaa atgaaggaat ctgcctacat ggagtcgacg    3780
tggggggcca agacagtagg ccccacggtg ccgtcggcat acctggacaa gcgcatcacc    3840
gacgatgtct cctatggctt ccacctctac accccgatga cggccacgac taaggcctgg    3900
ctggacgccc agcctccgcg ctccgtcacc tacgtatcct tcggcagcat ggccacgccg    3960
gggcccacgg agatggccga gatggccgag ggtctacata gcagcggcaa ggccttccta    4020
tgggttgtta gggcatcgga ggcctcaaag atccctgacg gattccagga aagggtgggt    4080
gggagaggac tcgtggtgac ctgggtggcg cagctggagg ttctagcaca cggcgccatc    4140
```

-continued

```
gggtgcttcg tgacgcactg tggatggaac tccacgatgg aggccctagg cgccggcgta   4200
ccgatggtgg cggtaccaca gtggtcggac cagcccacca acgccaagtt cgtcgaggac   4260
gtttggtgcg tcggcgtccg cgcccggcgg gatccggaag gggtggttag gagggaggag   4320
ttggagaggt gcattaggga ggtgacgggg gacgacaagt atgcatgcaa tgccttagat   4380
tggaaggaga aatcaaagag ggccatgtcc caaggggta gctcagacat gaacatcacg    4440
gaatttcttc aagcactaag aaggtcaaga aaatcatacg aggcgaaacc tatcgaacct   4500
ctgctggtgg ggttagatgc atgaataatc ttgggctaca cgggtgtttg agctacacgt   4560
caagatggga atgggcacga accgggcccc gttgccccag gaccaatctc aggggccaca   4620
gatcgatcca ttctcataaa atactatggc cctgctggcc tattgggtgc ccagggccga   4680
cccaattttc tgctagaata cactttttt aactctgtat acgcacgata atatgacata    4740
aatagaggtt acagaggaag tataaatcca attaacgata ttacaggttc aatgagcatc   4800
tacctaaata attcaaggag cacactacat ttcatgatca cctcagtata cgcatgataa   4860
tataaaataa atagaggttg cacaggaagt atacgtccat ccaattgatg atattacaag   4920
tttaataatt caagggacac actacattgc atcatctagc taaataattc agggaagatt   4980
attcaaggaa cacactacat ttcatcatct cctggaggta ctatacatcg ctcccacata   5040
gttcagtcat catcatcatc tatatttgga aaatacaaga attgttagag agcatcaaca   5100
acaattatat gcaagcaaaa tatcccttgc ttgatagatt tgcagtactc caggaagcat   5160
acatataaat tatgaatgat ttagctacat gcagtactac atgcagcgct cgaacaaaca   5220
gctaggaatc aactcactca tctagtgttt gaggtgactt cattttcact ctaattacat   5280
aagacatata aagatcacac attctatgat atgatattca tttggttcaa gaaaattctt   5340
ctttattagt aaaactgcta cttttaacaa tagagagtgt ttgcatgaaa acctggaatc   5400
tgactcactg tctccgatca actgaccaac taccagagca tgtggaggta ggaggcctag   5460
gctattatca cctatgcttg ccagcagcgc acggcaggtt actatccact gctcccgcct   5520
ctttgagtgt cctcatcatc tgcatttatc aaaatgatag aacatgaatt tgagtatatc   5580
agacaagacc acatagcata gtaagtaaaa atttgagcat agtatggttt atctacatgg   5640
acatatgttc aaattcagct tcaaagacag tcaaggacag agaaaacaag tacagttatc   5700
tttagacgtc atcgagtatg gggactacaa atttctaaca attacaatag gtgttaggta   5760
aagcaaagaa taatacagaa acatgtaaaa taccttctaa ctccattatt atgtgatgaa   5820
ttgagccatg ctacgctcac tattagttgc agaaaacaaa aacagatttt gatgaatgta   5880
aagtgcaagc ataataagaa acagaaaagc ttatgtttta tggctttata tgtggctctt   5940
atccagtcct gtagtcaaac aagagcttct gctgttttga gtgtcattca acttcaaaaa   6000
```

ENZYMES INVOLVED IN TRITERPENE SYNTHESIS

FIELD OF THE INVENTION

This invention is in the field of plant molecular biology. More specifically, this invention pertains to polynucleotides encoding enzymes involved in the biosynthesis of β-amyrin-derived triterpenes in plants and seeds. This invention also includes transgenic plants where the altered expression levels of the polynucleotides of the present invention results in altered levels or structures of β-amyrin-derived triterpenes, including saponins.

BACKGROUND OF THE INVENTION

The terpenoids, also called isoprenoids, constitute the largest family of natural products with over 22,000 individual compounds of this class having been described. The triterpenes or terpenoids (hemiterpenes, monoterpenes, sesquiterpenes, diterpenes, triterpenes, tetraterpenes, polyprenols, and the like) play diverse functional roles in plants as hormones, photosynthetic pigments, electron carriers, mediators of polysaccharide assembly, and structural components of membranes. The majority of plant terpenoids are found in resins, latex, waxes, and oils.

Triterpenoids are of relevance to a variety of plant characteristics, including palatability to animals, and resistance to pathogens and predators. Triterpenes are mostly stored in plant roots as their glycosides, saponins (see Price K. R. et al, 1987, *CRC Crit. Rev. Food Sci. Nutr.* 26:27-133). Thus, for example, mutants of the diploid oat species, *Avena strigosa*, which lack the major oat root saponin, avenacin A-1 (so called saponin-deficient or "Sad" mutants) have been shown to have compromised disease resistance (Papadopoulou K. et al., 1999, *Proc. Natl. Acad. Sci. U.S.A.* 96:12923-12928). These mutants have increased susceptibility to a number of different root-infecting fungi, including *Gaeumannomyces graminis* var. *tritici*, which is normally non-pathogenic to oats. Genetic analysis suggests that increased disease susceptibility and reduced avenacin content are causally related. Furthermore, a sad mutant which produces reduced avenacin levels (around 15% of that of the wild type) gives only limited disease symptoms when inoculated with *G. graminis* var. *tritici* in comparison to other mutants which lack avenacins completely, providing a further link between avenacin content and disease resistance.

There is an accumulating amount of data suggesting that saponins in the diet may be beneficial (see for example Shi, J. A. et al. (2004) *J. Med. Food* 7:67-78 and V is, E. H. et al. (2005) *Nutr. Cancer* 51:37-44). Similarly, dietary saponins of soybean have been shown to be beneficial in preventing hypercholesterolemia and aortic atherosclerosis in rats (Oakenfull, et al. (1984) Nutr. Rep. Int. 29:1039-1046). Since saponins are carried over from the bean into soy isolate with only minimal loss, increased levels of saponins in beans should lead to increased amounts of saponins in isolate (Berhow, M. A. et al. (2002) Phytochem. Anal. 13:343-348; Hu J., et al. (2002) J. Agric. Food Chem. 50:2587-2594). Increasing levels of saponins in beans, thus, would be an effective way of increasing saponin amounts in the human diet. In addition, the increase in saponins could provide a source for compounds used in drug development.

Triterpenes, as well as sterols, are synthesized via the isoprenoid pathway. In this pathway, two molecules of farnesyl pyrophosphate are joined head-to-head to form squalene, a triterpene. Squalene is then converted to 2,3-oxidosqualene. Various oxidosqualene cyclases catalyze the cyclization of 2,3-oxidosqualene to form various polycyclic skeletons, including one or more of cycloartenol, lanosterol, lupeol, isomultiflorenol, β-amyrin, α-amyrin, and thalianol.

This cyclization event catalyzed by oxidosqualene cyclases forms a branch point between the sterol and triterpene saponin biosynthetic pathways. The various oxidosqualene cyclases are evolutionarily related (Kushiro, T., et al. (1998) *Eur. J. Biochem.* 256:238-244) and produce a wide variety of three-, four-, and five-ring structures that can be further modified.

Triterpenoid saponins are synthesized via the isoprenoid pathway by cyclization of 2,3-oxidosqualene to give pentacyclic triterpenoids, primarily oleanane (β-amyrin) or damarane skeletons. The triterpenoid backbone then undergoes various modifications (oxidation, substitution, and glycosylation), mediated by cytochrome P450-dependent monooxygenases, glycosyltransferases (GTs), and other enzymes. In general very little is known about the enzymes and biochemical pathways involved in saponin biosynthesis. The genetic machinery required for the elaboration of this important family of plant secondary metabolites is as yet largely uncharacterized, despite the considerable commercial interest in this important group of natural products. This is likely to be due in part to the complexity of the molecules and the lack of pathway intermediates for biochemical studies. However, the first dedicated step in saponin biosynthesis is now understood to be carried out by the oxidosqualene cyclase β-amyrin synthase (the product of the Sad1 gene), which has recently been cloned and characterized (Haralampidis K. et al., 2001, *Proc. Natl. Acad. Sci. U.S.A.* 98:13431-13436). Another key step, mediated by the cytochrome P450 enzyme AsCYP51H10 (encoded by the Sad2 gene), has also recently been studied (Qi X. et al., 2006, Proc. Natl. Acad. Sci. U.S.A 103:18848-18853). AsCYP51H10 (SAD2) is required for avenacin synthesis. The precise biochemical function of AsCYP51H10 is not known. However Sad2 mutants accumulate β-amyrin and so AsCYP51H10 is likely to be required for oxidation of β-amyrin (or a derivative of this) at one or more positions (C12, C13, C16, C21 and/or C30) (FIG. 1).

Structural comparisons (FIG. 1) predict that other classes of enzyme in addition to cytochrome P450s will also be required for conversion of β-amyrin to avenacin A-1. These include glycosyltransferases (GTs), acyl transferases, and methyl transferases (MTs). Glycosyltransferases belong to a large family of enzymes that transfer saccharide units from activated donor molecules onto a wide spectrum of potential acceptor molecules. The array of potential acceptors includes proteins, lipids, polysaccharides and small molecules, which may be involved in diverse cellular processes such as cell wall synthesis and signalling (Coutinho P M et al., 2003, J. Mol. Biol., 328:307-317). Of seventy-seven GT families with representatives spanning all Kingdoms, the GT Family 1 is one of the largest (Coutinho P M and Henrissat B, 1999: Carbohydrate active enzymes website http://afmb.cnrs-mrs.fr/CAZY/). Family 1 consists of GTs that operate via an inverting catalytic mechanism of sugar transfer, usually onto low molecular weight acceptor molecules (Vogt T and Jones P, 2000, Trends Plant Sci. 5:380-386; Lim E-K and Bowles D J, 2004, EMBO J. 23:2915-2922). The branched sugar chain of avenacin A-1 is predicted, by analogy to other glycosylated small molecules, to be synthesized by the sequential addition of sugar units onto the aglycone component, most probably by the activity of three different glycosyltransferases (GTs). The first step in glycosylation involves the addition of L-arabinose onto the C3 hydroxyl group of the aglycone, mediated by an arabinosyltransferase. This is followed by the addition of two D-glucose molecules, one at the C2 position of the arabinose and the other at the C4 position, mediated by one (or possibly two) glucosyltransferases (Townsend B et al., 2006, Phytochemistry Revs. 5:109-114).

Acylation is a common feature of plant-derived natural products and alters their chemical and physical properties. It is therefore likely to influence the biological effects of natural products in ecological interactions and to influence other key processes such as subcellular trafficking and sequestration (for example by serving as a vacuolar uptake or retention tag). A new class of plant acyltransferases has recently been discovered. These enzymes—serine carboxypeptidase-like acyl tranferases—share homology with peptidases but lack peptidase activity and instead are able to acylate natural products (Milkowski C & Strack D (2003) Phytochemistry 65: 517; Fraser C M et al. (2005) Plant Physiology 138:1136). While other plant acyltransferases commonly use coenzyme thioesters as acyl donors these SCPLs use acyl glucose donors. The best-characterized members of the SCPL acyltransferase family are the tomato enzyme GAC-Lp, which catalyses the formation of glucose polyesters that contribute to insect resistance in wild tomato (Li A X & Steffens J C, 2000, PNAS 97: 6902); the *Arabidopsis* enzyme SNG1, which is required for the synthesis of the phenylpropanoid sinapoylmalate (a UV protectant) (Landry L G et al., 1995, Plant Physiology 109:1159; Lehfeldt C et al., 2000, Plant Cell 12:1295); a second *Arabidopsis* enzyme SNG2, which is involved in synthesis of sinapoyl choline in the seeds (Shirley A M et al., 2001, Plant J 28:83); and the *Brassica napus* acyltransferase BnSCT, which catalyses the formation of sinapate esters associated with bitterness, astringency and seed oil extraction problems (Milkowski C et al., 2004, Plant J. 38:80; Baumert A et al., 2005, Phytochemistry 66:1334). Many other important plant-derived natural products are known from biochemical analysis to be produced by glucose-ester-dependent acyltransferase reactions although the enzymes and genes involved in these modifications have not been characterized. Examples include the antioxidant chlorogenic acid in sweet potato (*Ipomoea batatas*), anthocyanins in wild carrot (*Daucus carota*), gallotannins in oak (*Quercus robur*) and sinapoyl- and benzoyl-esterified glucosinolates in brassicas (Milkowski C & Strack D (2003) Phytochemistry 65: 517; Fraser C M et al. (2005) Plant Physiology 138:1136). There are four different structurally related avenacins [14]. Avenacins A-1 (the major avenacin found in oat roots) and B-1 are acylated with N-methyl anthranilic acid, and avenacins A-2 and B-2 with benzoic acid (Hostettmann K and Marston A, 1995, Saponins, Cambridge University Press, Cambridge, UK).

S-Adenosyl-L-methionine-dependent methyltransferases are involved in O-methylation of many plant natural products (Frick S. et al. 2001, Phytochemistry 56:1-4). These enzymes play important roles in the synthesis of lignin precursors and other compounds required for plant defense (Gang D R et al 2002, Plant Cell 14:505-519.

SUMMARY OF THE INVENTION

The instant invention relates to isolated polynucleotides encoding enzymes involved in triterpene synthesis. Specifically, this invention concerns isolated polynucleotides encoding a novel serine carboxypeptidase-like acyl transferase, a novel methyltransferase, and a novel family 1 glucosyltransferase. These novel enzymes isolated from *Avena strigosa* are referred to as AsSCPL1 (serine carboxypeptidase-like acyl transferase), AsMT1 (methyltransferase) and AsGT2 (glucosyltransferase).

Identification of the genes encoding enzymes responsible for triterpene synthesis in a variety of crops will allow their manipulation. Manipulation of triterpene synthesis will result in changes in the levels or structures of the triterpene saponins. An increase in saponin production will result in an enhancement of plant resistance to pests. Foods originating from plants having an increased level of triterpenes are thought to have a cholesterol lowering effect while decreased triterpenes are believed to result in better tasting foods having. Thus, transgenic plants having altered levels of triterpenes may be resistant to pests and foods prepared with seeds having altered levels or structures of saponins will have increased nutritional value or better flavor.

In another embodiment, the instant invention relates to an isolated polynucleotide comprising a nucleotide sequence encoding a serine carboxypeptidase-like acyl transferase polypeptide having an amino acid sequence of at least 95% sequence identity, based on the Clustal V method of alignment, when compared to SEQ ID NO:2; or a nucleotide sequence encoding a methyltransferase polypeptide having an amino acid sequence of at least 95% sequence identity, based on the Clustal V method of alignment, when compared to SEQ ID NO:4; or a nucleotide sequence encoding a glucosyltransferase having an amino acid sequence of at least 95% sequence identity, based on the Clustal V method of alignment, when compared to SEQ ID NO:6; or a nucleotide sequence comprising the full complement of (a), (b) or (c).

In another embodiment, the instant invention relates to a vector comprising the isolated polynucleotides of the present invention.

In a further embodiment, the instant invention relates to a recombinant DNA construct comprising at least a portion of the polynucleotides of the present invention, encoding a first enzyme of the triterpene pathway, operably linked to at least one regulatory sequence.

In another embodiment, the instant invention relates to a recombinant DNA construct comprising at least a portion of the polynucleotides of the present invention, encoding a first enzyme of the triterpene pathway, operably linked to at least one regulatory sequence and further comprising at least a portion of at least a second polynucleotide encoding a polypeptide that regulates expression of at least a second enzyme of the triterpene pathway.

In another embodiment, the instant invention concerns an isolated host cell comprising the recombinant DNA constructs of the present invention. The host cell may be a yeast cell, bacterial cell, or a plant cell.

Compositions, including plants and plant parts, comprising the isolated polypeptides or polynucleotides of the present invention are also embodied by the present invention. The invention also includes transformed plants that arise from transformed host cells of higher plants and seeds or grains derived from such transformed plants. Such transgenic plants include those having an altered level of β-amyrin-derived triterpenes, or triterpenes with altered modifications.

In another embodiment, the instant invention concerns a transgenic plant comprising a recombinant of the present invention wherein the regulatory sequence is a heterologous promoter wherein the transgenic plant has an altered level of a triterpene when compared to a plant having wild type level of triterpene.

The present invention also relates to a method of altering the level of expression of a polypeptide in a plant cell comprising: transforming plant tissue with a nucleic acid fragment from at least a portion of the isolated polynucleotide of the present invention, wherein said polynucleotide is capable of altering expression of native serine carboxypeptidase-like acyl transferase, methyltransferase, or glucosyltransferase; regenerating said plant tissue into a transgenic plant; and evaluating said transgenic plant for altered level of expression of serine carboxypeptidase-like acyl transferase, methyltransferase, or glucosyltransferase when compared to a plant having wild type level of expression of corresponding native serine carboxypeptidase-like acyl transferase, methyltransferase, or glucosyltransferase.

The present invention also relates to a method of producing a plant resistant to at least one fungus comprising: transforming a plant cell with at least one recombinant DNA construct of the present invention encoding a first enzyme of the triterpene pathway; growing the transformed plant cell from step (a) under conditions that promote the regeneration of a transgenic plant; and evaluating the transgenic plant of step (b) for increased resistance to at least one fungus when compared to a plant of the same species that is not transformed with said recombinant DNA construct. The recombinant construct may further comprise at least a second polynucleotide encoding a polypeptide that regulates expression of at least a second enzyme of the triterpene pathway which is expected to include but not limited to the polynucleotides of the present invention as well as nucleotide sequences encoding the enzymes of the first two steps in the pathway, the oxidosqualene cyclase β-amyrin synthase (the product of the Sad1 gene; Haralampidis K. et al., 2001, Proc. Natl. Acad. Sci. U.S.A. 98:13431-13436) and/or the cytochrome P450 enzyme CYP51H10 (encoded by the Sad2 gene; Qi X. et al., 2006, Proc. Natl. Acad. Sci. U.S.A. 103:18848-18853).

The present invention in also directed to a method of producing a plant with altered levels of serine carboxypeptidase-like acyl transferase, methyltransferase, or glucosyltransferase comprising: transforming a plant cell with at least one recombinant DNA construct of claim 5 encoding a first enzyme of the triterpene pathway; growing the transformed plant cell from step (a) under conditions that promote the regeneration of a transgenic plant; and evaluating the transgenic plant of step (b) for an altered level of serine carboxypeptidase-like acyl transferase, methyltransferase, or glucosyltransferase when compared to the amount of serine carboxypeptidase-like acyl transferase, methyltransferase, or glucosyltransferase in a plant of the same species that is not transformed with said recombinant DNA construct.

The present invention also relates to a method for producing a plant with an altered level of triterpene saponin comprising: transforming a plant cell with at least one recombinant DNA construct of the present invention encoding a first enzyme of the triterpene pathway; growing the transformed plant cell from step (a) under conditions that promote the regeneration of a transgenic plant; and evaluating the transgenic plant of step (b) for an altered level of triterpene saponin when compared to the amount of triterpene saponin in a plant of the same species that is not transformed with said recombinant DNA construct. The recombinant construct may further comprise at least a portion of at least a second polynucleotide encoding a polypeptide that regulates expression of at least a second enzyme of the triterpene pathway which is expected to include but not limited to the polynucleotides of the present invention (acyltransferase, methyltransferase and glucosyltransferase), Sad1 and Sad2.

The present invention in also directed to a method for producing a plant with an increased level of triterpene saponin comprising: transforming a plant cell with at least one recombinant DNA construct of claim 5 encoding a first enzyme of the triterpene pathway; growing the transformed plant cell from step (a) under conditions that promote the regeneration of a transgenic plant; and evaluating the trans- genic plant of step (b) for an increased level of triterpene saponin when compared to the amount of triterpene saponin in a plant of the same species that is not transformed with said recombinant DNA construct. The recombinant construct may further comprise at least a second polynucleotide encoding a polypeptide that regulates expression of at least a second enzyme of the triterpene pathway which is expected to include but not limited to the polynucleotides of the present invention (acyltransferase, methyltransferase and glucosyltransferase), Sad1 and Sad2.

The present invention also relates to a method for producing a plant with a decreased level of triterpene saponin comprising: transforming a plant cell with at least one recombinant DNA construct of the present invention encoding a first enzyme of the triterpene pathway; growing the transformed plant cell from step (a) under conditions that promote the regeneration of a transgenic plant; and evaluating the transgenic plant of step (b) for a decreased level of triterpene saponin when compared to the amount of triterpene saponin in a plant of the same species that is not transformed with said recombinant DNA construct. The recombinant construct may further comprise at least a portion of at least a second polynucleotide encoding a polypeptide that regulates expression of at least a second enzyme of the triterpene pathway which is expected to include but not limited to the polynucleotides of the present invention (acyltransferase, methyltransferase and glucosyltransferase), Sad1 and Sad2.

Also included in the invention are the grains from the transgenic plants of the invention.

BRIEF DESCRIPTION OF THE DRAWINGS AND SEQUENCE LISTING

The invention can be more fully understood from the following detailed description and the accompanying drawings and Sequence Listing, which form a part of this application.

Figure 3:
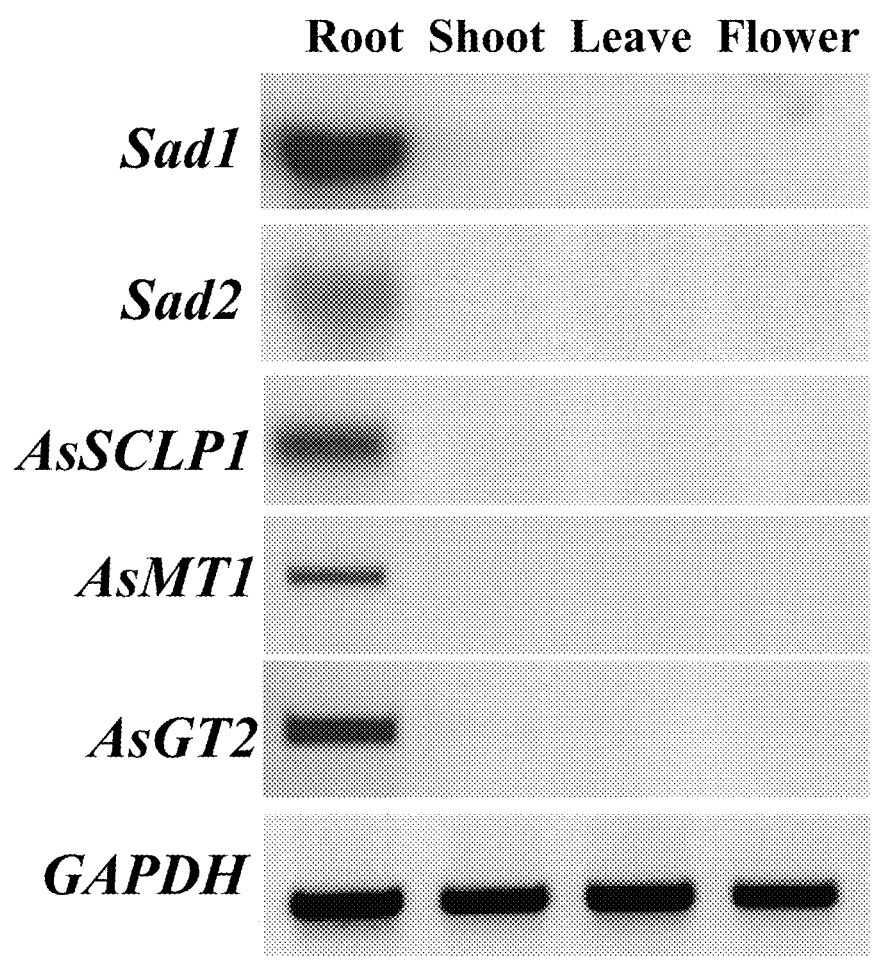

FIG. 3 Northern blot analysis for five predicted biosynthetic enzymes (beta-amyrin synthase (SAD1), cytochrome P450 CYP51H10 (SAD2), the serine carboxypeptidase-like protein AsSCPL1, the methyltransferase AsMT1, the glucosyltransferase AsGT2 and the GAPDH control) in root shoot, leaf and flower tissue of Oat.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

SEQ ID NO:1 is the nucleotide sequence of the cDNA encoding the serine carboxypeptidase-like polypeptide from *Avena strigosa* (AsSCPL1).

SEQ ID NO:2 is the amino acid sequence of AsSCPL1 derived from the cDNA fragment shown in SEQ ID NO:1 or the genomic fragment shown in SEQ ID NO:7.

SEQ ID NO:3 is the nucleotide sequence of the cDNA encoding the acyl methyltransferase from *Avena strigosa* (AsMT1).

SEQ ID NO:4 is the amino acid sequence of AsMT1 derived from the cDNA fragment shown in SEQ ID NO:3 or the genomic fragment shown in SEQ ID NO:8.

SEQ ID NO:5 is the nucleotide sequence of the cDNA encoding the glucosyltransferase from *Avena strigosa* (AsGT2).

SEQ ID NO:6 is the amino acid sequence of AsGT2 derived from the cDNA fragment shown in SEQ ID NO:5 or the genomic fragment shown in SEQ ID NO:9.

SEQ ID NO:7 is the nucleotide sequence of the genomic fragment encoding AsSCPL1.

SEQ ID NO:8 is the nucleotide sequence of the genomic fragment encoding AsMT1.

SEQ ID NO:9 is the nucleotide sequence of the genomic fragment encoding AsGT2.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms and abbreviations are used. The following definitions are provided.

"Open reading frame" is abbreviated ORF.

"Polymerase chain reaction" is abbreviated PCR.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridylate, "T" for deosythymidylate, "R" for purines (A or G), "Y" for pyrimidiens (C or T), "K" for G or T, "H" for A or C or T, "I" for inosine, and "N" for any nucleotide.

The term "isolated" polynucleotide is one that has been substantially separated or purified from other polynucleotides of the organism in which the polynucleotide naturally occurs, i.e., other chromosomal and extrachromosomal DNA and RNA, by conventional nucleic acid purification methods. The term also embraces recombinant polynucleotides and chemically synthesized polynucleotides. An isolated polynucleotide of the present invention may include all or part of the isolated polynucleotide, such as for example a polynucleotide comprising the nucleotide sequence selected from the group consisting of SEQ ID NO:1, SEQ ID NO:3, SEQ ID NO:5, SEQ ID NO:7, SEQ ID NO:8 and SEQ ID NO:9 or the full complement of such nucleotide sequences.

Triterpenoid saponins are synthesized via the isoprenoid pathway by cyclization of 2,3-oxidosqualene to give pentacyclic triterpenoids, primarily oleanane (β-amyrin) or dammarane skeletons. The triterpenoid backbone then undergoes various modifications, including oxidation, acylation, methylation, glycosylation and other substitutions, mediated by cytochrome P450-dependent monooxygenases, glycosyltransferases, acyl transferases, methyltransferases and other enzymes.

Triterpenes, also known as triterpenoids, include and are not limited to sapinogenins and sterols.

"Saponins" refers to the glycoside conjugates of cyclized triterpenes that naturally accumulate in plants. Cyclized triterpenes include, and are not limited to, lanosterol, cycloartenol, β-amyrin, α-amyrin, lupeol, isomultiflorenol, and thalianol. "Triterpene saponins" refers to the glycoside conjugates of cyclized triterpenes excluding those derived from lanosterol or cycloartenol. "Steroidal saponins" refer to the glycoside conjugates derived from lanosterol or cycloartenol. Sapogenols are derived from triterpene saponins via in vitro acid hydrolysis and their measurement provides a relative value for the amount of triterpene saponins present in the tissue from which the saponins are extracted.

The level of triterpene saponins can be determined by measurement of sapogenols. Measurement of sapogenols directly correlates to the level of triterpene saponins. Sapogenols are derived from triterpene saponins via in vitro acid hydrolysis and their measurement provides a relative value which can be directly correlated into the amount of triterpene saponins present in the tissue from which the saponins are extracted.

The triterpene saponin levels can be measured using techniques known in the art. For example, one could use HPLC-MS or HPLC with a light scattering detector (see for example Rupasinghe, H. P. et al, (2003) J. Agri. Food Chem. 51:5888-5894). Alternatively, one could use HPLC with a UV detector (Hubert J, et al. (2005) J. Agric. Food Chem. 53:3923-3930). Other methods include using GC-FAB. (see for example Gee et al. (1993) J Sci Food Agric. 63:201-209). Other methods involve separating saponins using thin layer chromatography (TLC) coupled with densitometry (see for example Oleszek W A. (2002) J. Chromatogr. A 967:147-162.; Gurfinkel D M, and Rao A V (2002) J. Agric. Food Chem. 50:426-430.

It may also be possible to measure triterpene saponins using other methods. For example, methods using various immunoassays (e.g., a radioimmunoassay or ELISA) may be adapted (Wang C C, Prasain J K, and Barnes S. (2002) J. Chromatogr. B Analyt. Technol. Biomed. Life Sci. 777:3-28, Ahamed A et al. (2003) Biochem. Biophys. Res. Commun. 302:587-592).

The "increased triterpene saponin levels," for purposes of the present invention refer to triterpene saponin levels higher than those found in non-transformed plants of the same species resulting from a transferred nucleic acid fragment of the invention. For example, "increased triterpene saponin levels," may refer to triterpene saponin levels higher than those found in plants of the same species not having the recombinant DNA molecule of the invention comprising a polynucleotide encoding an oxidosqualene cyclase. The "increased triterpene saponin levels" levels may be at least 100 ppm higher, 250 ppm higher, 500 ppm higher, 750 ppm higher, 1000 ppm higher, 1250 ppm higher, 1500 ppm higher, 3000 ppm higher, 6000 ppm higher, or any integer thereof.

"Altered levels" or "altered expression" refers to the production of gene product(s) in transgenic organisms in amounts or proportions that differ from that of normal or non-transformed organisms.

An "altered level if triterpene saponin," for purposes of the present invention refer to triterpene saponin levels in amounts or proportions that differ from those found in non-transformed plants of the same species not having resulting from a transferred nucleic acid fragment of the invention.

The "decreased triterpene saponin levels," for purposes of the present invention refer to triterpene saponin levels lower than those found in non-transformed plants of the same species not having resulting from a transferred nucleic acid fragment of the invention.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., Anal. Biochem. 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS*. 5:151-153 (1989); Higgins, D. G. et al. (1992) *Comput. Appl. Biosci.* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequence encoding the AsSCPL1, AsMT1 and AsGT2 proteins as set forth in SEQ ID NO:2, SEQ ID NO:4, and SEQ ID NO:6. The skilled artisan is well aware of the "codon-bias" exhibited by a specific host cell in usage of nucleotide codons to specify a given amino acid. Therefore, when synthesizing a polynucleotide for improved expression of a specific gene in a host cell, it is desirable to design the polynucleotide such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well-established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" as it applies to a plant cells encompasses not only chromosomal DNA found within the nucleus, but organelle DNA found within subcellular components (e.g., mitochondrial, plastid) of the cell.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. Plant Cell 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro.

"Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved.)

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into ac ell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

A "signal peptide" is an amino acid sequence that is translated in conjunction with a protein and directs the protein to the secretory system (Chrispeels, M. (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel, N. (1992) *Plant Phys.* 100:1627-1632). A "chloroplast transit peptide" is an amino acid sequence that is translated in conjunction with a protein and directs the protein to the chloroplast or other plastid types present in the cell in which the protein is made. "Chloroplast transit sequence" refers to a nucleotide sequence that encodes a chloroplast transit peptide.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "suppression" refers to the reduction of the level of enzyme activity detectable in a transgenic plant when compared to the level of enzyme activity detectable in a plant with the native enzyme. The level of enzyme activity in a plant with the native enzyme is referred to herein as "wild type" activity. The term "suppression" includes lower, reduce, decline, decrease, inhibit, eliminate and prevent. This reduction may be due to the decrease in translation of the native mRNA into an active enzyme. It may also be due to the transcription of the native DNA into decreased amounts of mRNA and/or to rapid degradation of the native mRNA. The term "native enzyme" refers to an enzyme that is produced naturally in the desired cell.

Suppression of enzymes in plants may be accomplished by any one of many methods known in the art which include the following. "Cosuppression" refers to the production of sense RNA transcripts capable of suppressing the expression of identical or substantially similar native genes (U.S. Pat. No. 5,231,020). Co-suppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) Plant J. 16:651-659; and Gura (2000) Nature 404:804-808). "Antisense inhibition" refers to the production of antisense RNA transcripts capable of suppressing the expression of the target protein. Plant viral sequences may be used to direct the suppression of proximal mRNA encoding sequences (PCT Publication WO 98/36083 published on Aug. 20, 1998). "Hairpin" structures that incorporate all, or part, of an mRNA encoding sequence in a complementary orientation resulting in a potential "stem-loop" structure for the expressed RNA have been described (PCT Publication WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286. A construct where the stem is formed by at least 30 nucleotides from a gene to be suppressed and the loop is formed by a random nucleotide sequence has also effectively been used for suppression (WO 99/61632 published on Dec. 2, 1999). The use of poly-T and poly-A sequences to generate the stem in the stem-loop structure has also been described (WO 02/00894 published Jan. 3, 2002). Yet another variation includes using synthetic repeats to promote formation of a stem in the stem-loop structure. Transgenic organisms prepared with such recombinant DNA fragment show reduced levels of the protein encoded by the polynucleotide from which the nucleotide fragment forming the loop is derived as described in PCT Publication WO 02/00904, published Jan. 3, 2002. The use of constructs that result in dsRNA has also been described. In these constructs convergent promoters direct transcription of gene-specific sense and antisense RNAs inducing gene suppression (see for example Shi, H. et al. (2000) RNA 6:1069-1076; Bastin, P. et al. (2000) J. Cell Sci. 113:3321-3328; Giordano, E. et al. (2002) Genetics 160: 637-648; LaCount, D. J. and Donelson, J. E. US patent Application No. 20020182223, published Dec. 5, 2002; Tran, N. et al. (2003) BMC Biotechnol. 3:21; and Applicant's U.S. Provisional Application No. 60/578,404, filed Jun. 9, 2004).

Other methods for suppressing an enzyme include, but are not limited to, use of polynucleotides that may form a catalytic RNA or may have ribozyme activity (U.S. Pat. No. 4,987,071 issued Jan. 22, 1991), and micro RNA (also called miRNA) interference (Javier et al. (2003) Nature 425:257-263).

The sequences of the polynucleotide fragments used for suppression do not have to be 100% identical to the sequences of the polynucleotide fragment found in the gene to be suppressed. For example, suppression of all the subunits of the soybean seed storage protein β-conglycinin has been accomplished using a polynucleotide derived from a portion of the gene encoding the α subunit (U.S. Pat. No. 6,362,399). β-conglycinin is a heterogeneous glycoprotein composed of varying combinations of three highly negatively charged subunits identified as α, α' and β. The polynucleotide sequences encoding the α and α' subunits are about 85% identical to each other while the polynucleotide sequences encoding the β subunit are about 75 to about 80% identical to the α and α' subunits, respectively. Thus, polynucleotides that are at least about 75% identical to a region of the polynucleotide that is target for suppression have been shown to be effective in suppressing the desired target. The polynucleotide may be at least about 80% identical, at least about 90% identical, at least about 95% identical, or about 100% identical to the desired target sequence.

A "portion capable of suppressing expression" of a native gene refers to a portion or subfragment of an isolated nucleic acid fragment in which the ability to alter gene expression or produce a certain phenotype is retained whether or not the fragment or subfragment may be translated into an active enzyme. For example, the fragment or subfragment may be used in the design of chimeric genes or recombinant DNA fragments to produce the desired phenotype in a transformed plant. Chimeric genes may be designed for use in suppression by linking a nucleic acid fragment or subfragment thereof, whether or not it is translated into an active enzyme, in the sense or antisense orientation relative to a plant promoter sequence. Recombinant DNA fragments may be designed to comprise nucleic acid fragments capable of promoting formation of a stem-loop structure. In a stem-loop structure either the loop or the stem comprises a portion of the gene to be suppressed. The nucleic acid fragment should have a stretch of at least about 20 contiguous nucleotides that are identical to the gene to be suppressed. The stretch of contiguous nucleotides may be any number, from at least about 20, or about 32, to the size of the entire gene to be suppressed.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

A "plant resistant to at least one fungus" refers to a plant comprising a recombinant DNA construct of the present invention which when infected with a fungus is able to resist infection or to tolerate infection to a greater degree, resulting in less damage, more vigorous health and less or no loss of yield due to fungal infection relative to plants without the recombinant DNA construct of the present invention. The fungus is typically pathogenic. "Pathogenic" or "fungal pathogen" refer to a fungus that under conditions that do not include the recombinant DNA construct of the present invention, would cause disease in a plant. A transgenic plant comprising the recombinant DNA construct of the present invention is typically a plant more resistant to at least one fungus than a plant of the same species without the recombinant DNA construct of the present invention.

Plant Expression Systems, Cassettes and Vectors, and Transformation

A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, the Kunitz trypsin inhibitor 3 promoter, the annexin promoter, the glycinin Gy1 promoter, the beta subunit of beta conglycinin promoter, the P34/Gly Bd m 30K promoter, the albumin promoter, the Leg A1 promoter and the Leg A2 promoter.

The annexin, or P34, promoter is described in PCT Publication No. WO 04/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J Biol. Chem.* 265(21):12486-93 (1990)); (4) a tomato ubiquitin gene promoter (Rollfinke et al., *Gene.* 211(2):267-76 (1998)); (5) a soybean heat shock protein promoter (Schoffl et al., *Mol Gen Genet.* 217(2-3): 246-53 (1989)); and, (6) a maize H3 histone gene promoter (Atanassova et al., *Plant Mol Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual;* $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology;* John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation).

The recombinant constructs of the invention may be introduced into one plant cell; or, alternatively, each construct may be introduced into separate plant cells.

Expression in a plant cell may be accomplished in a transient or stable fashion as is described above.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci. U.S.A.* 84:3962-3966 (1987)), microinjection and particle bombardment (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

The present invention is directed to isolated polynucleotides encoding a serine carboxypeptidase-like acyl transferase, a methyltransferase, or a glucosyltransferase. As used herein "polynucleotides" refers to polynucleotides that encode novel serine carboxypeptidase-like acyl transferase, methyltransferase, or a glucosyltransferase enzymes involved in the biosynthesis of β-amyrin-derived triterpenes in plants or triterpenes with altered modifications. These enzymes isolated from *Avena strigosa* are referred to as AsSCPL1 (a serine carboxypeptidase-like acyl transferase), AsMT1 (a methyltransferase) and AsGT2 (a glucosyltransferase).

Sad7 mutants fail to produce avenacins and accumulate triterpene glycosides with a hydroxyl in place of the N-methyl anthranilate (avenacins A-1 and B-1) or benzoate (avenacins A-2 and B-2) acyl groups (Qi X et al. 2004, *Proc. Natl. Acad. Sci. U.S.A.* 101:8233). They are therefore compromised in triterpene acylation. Four mutations conferring a Sad7 phenotype have been identified (Table 1). Each of these has a lesion in the polynucleotide of the present invention that would render the polynucleotide incapable of expressing a functional mRNA encoding a functional protein. These data together with the biochemical data presented herein indicate that the non-mutated polynucleotide of the present invention encodes the enzyme serine carboxypeptidase-like acyl transferase from *Avena strigosa* (ASCPL1) responsible for acylation of the triterpene backbone, which is not carried out in the Sad7 mutants. cDNA and genomic fragments encoding AsSCPL1 are disclosed (SEQ ID NO:1 and SEQ ID NO:7).

TABLE 1

Characterization of Sad7 mutants. The position of the base change shown (superscript $2^{nd}$ column) is based on comparison of the mutant DNA sequence with SEQ ID NO: 1.

| Mutants | Base Change | | Predicted amino acid change | |
|---|---|---|---|---|
| 19.1 | $C^{1443}$ | T | $Thr^{463}$ | Ile |
| 587 | $C^{465}$ | T | $Ser^{137}$ | Phe |
| 616 | $C^{465}$ | T | $Ser^{137}$ | Phe |
| 376 | $C^{291}$ | T | $Pro^{79}$ | Leu |

Figure 1:
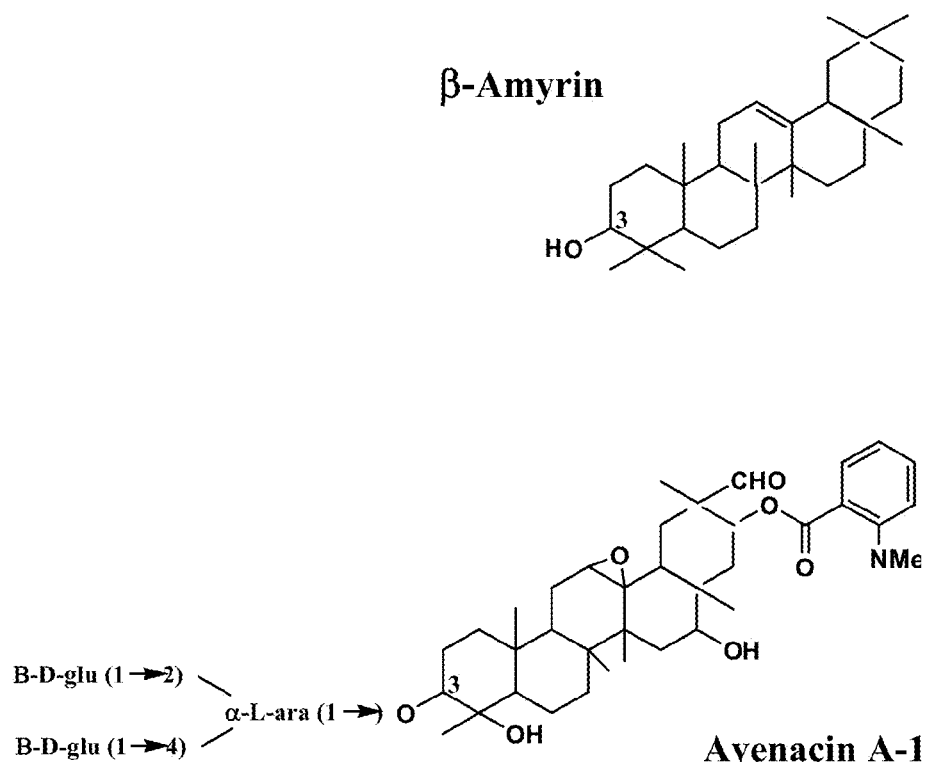
FIG. 1 depicts the structures of β-amyrin and Avenacin A-1 highlighting the multiple modifications that must take place to derive the latter from the former.

The Sad9 gene product shares homology with methyltransferases involved in phenylpropanoid biosynthesis, including a barley methyltransferase that is induced in leaves in response to pathogen attack and UV stress (Christensen A et al., 1998, Plant Mol. Biol. 36:219). Since this methyltransferase is required for avenacin synthesis its role is likely to be in methylation of the anthranilate moiety of avenacins A-1 and B-1 (FIG. 1). Four mutations conferring a Sad9 phenotype have been identified (Table 2). Each of these has a lesion in the polynucleotide of the present invention that would render the polynucleotide incapable of expressing a functional mRNA encoding a functional protein. These data together with the biochemical data presented herein indicate that the non-mutated polynucleotide of the present invention encodes the methyltransferase from *Avena strigosa* (AsMT1) responsible for methylation of the anthranilate moiety of avenacins A-1 and B-1. cDNA and genomic fragments encoding AsMT1 are disclosed (SEQ ID NO:3 and SEQ ID NO:8).

TABLE 2

Characterization of Sad9 mutants. The position of the base change shown (superscript $2^{nd}$ column) is based on comparison of the mutant DNA sequence with SEQ ID NO: 3.

| Mutants | Base Change | | Predicted amino acid change | |
|---|---|---|---|---|
| 195 | $G^{974}$ | A | $Arg^{321}$ | Glu |
| 961 | $C^{101}$ | T | $Ser^{30}$ | Phe |
| 841 | $C^{1010}$ | T | $Ala^{333}$ | Val |
| 1310 | $G^{990}$ | A | $Try^{326}$ | stop |

The Sad10 glucosyltransferase, shares homology with enzymes that glucosylate salicylic acid and other benzoic acid derivatives. The cDNA and genomic fragments encoding a glucosyltransferase from *Avena strigosa* (AsGT2) are disclosed (SEQ ID NO:5 and SEQ ID NO:9).

Identification of the genes encoding enzymes responsible for triterpene synthesis in a variety of crops will allow their manipulation. Manipulation of triterpene synthesis will result in changes in the levels or structures of the triterpene saponins.

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other acyl transferases (in particular those of the serine carboxy peptidase-like class), glucosyltransferases or methyltransferases, either as cDNAs or genomic DNAs, may be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Sambrook et al., Molecular Cloning: A Laboratory Manual, Cold Spring Harbor: NY (1989)). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full-length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., 1988, *Proc. Natl. Acad. Sci. U.S.A.* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., 1989, *Proc. Natl. Acad. Sci. U.S.A* 86:5673-5677; Loh et al., 1989, *Science* 243:217-220). Products generated by the 3' and 5' RACE procedures can be combined to generate full-length cDNAs (Frohman and Martin, 1989, *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, 1984, *Adv. Immunol.* 36:1-34; Sambrook).

Plasmid vectors comprising the isolated polynucleotide of the invention may be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., 1985, *EMBO J.* 4:2411-2418; De Almeida et al., 1989, *Mol. Gen. Genetics* 218:78-86), and thus that multiple events may have to be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the recombinant DNA constructs of the present invention may be further supplemented by altering the coding sequence to encode appropriate intracellular targeting signals such as transit signals (Keegstra, 1989, *Cell* 56:247-253), signal sequences with or without endoplasmic reticulum retention signals (Chrispeels, 1991, *Ann. Rev. Plant Phys. Plant Mol. Biol.* 42:21-53), or nuclear localization signals (Raikhel, N., 1992, *Plant Phys.* 100:1627-1632) with or without removing targeting signals that are already present. While the references cited give examples of each of these, the list is not exhaustive and more targeting signals of utility may be discovered in the future.

Expression of a chimeric serine carboxypeptidase-like acyl transferase, methyltransferase, or glucosyltransferase, for example, respectively results in the production of a level of the encoded serine carboxypeptidase-like acyl transferase, methyltransferase, or glucosyltransferase protein in a transformed host cell that is altered as compared to the level produced in an untransformed host cell. Also, a transgenic plant, or plant part, comprising a polynucleotide of the present invention, such as for example, SEQ ID NO:1, SEQ ID NO:3, and SEQ ID NO:5, SEQ ID NO:7, SEQ ID NO:8, and SEQ ID NO:9 under the control of a heterologous promoter results in plants having altered levels of triterpenes. Plants may be selected from the group consisting of monocots and dicots. Monocots include and are not limited to corn, oat, rice, wheat, barley, palm, and the like. Dicots include and are not limited to *Arabidopsis*, soybean, oilseed *Brassica*, peanut, sunflower, safflower, cotton, tobacco, tomato, potato, cocoa, and the like. Plant parts include and are not limited to seeds and grains, for example. Thus, isolated polynucleotides of the present invention can be incorporated into recombinant constructs capable of introduction into and replication in a host cell.

Thus, this invention also concerns a method for transforming a cell, comprising transforming a cell with the recombinant construct of the invention and selecting those cells transformed with one of the recombinant constructs of the invention. Also of interest is a method for producing a transformed plant comprising transforming a plant cell with the polynucleotides of the instant invention and regenerating a plant from the transformed plant cell.

The nucleic acid fragments of the instant invention may be used to create transgenic plants in which the acyl transferases, glucosyltransferases or methyltransferases of the present invention are present at higher levels than normal or in cell types or developmental stages in which they are not normally found. This would have the effect of altering production of triterpenes in those cells. It is believed that overexpression of the polynucleotides of the invention, optionally in combination with polynucleotides encoding enzymes responsible for other steps in the saponin biosynthetic pathway, enhances resistance to at least one fungus.

Overexpression of serine carboxypeptidase-like acyl transferases, glucosyltransferases or methyltransferases of the instant invention may be accomplished by first constructing a recombinant DNA construct in which the coding region is operably linked to a promoter capable of directing expression of a first enzyme of the triterpene pathway such as a serine carboxypeptidase-like acyl transferases, a glucosyltransferase or a methyltransferase of the instant invention in the desired tissues at the desired stage of development. The recombinant DNA construct may comprise promoter sequences and translation leader sequences derived from the same genes. 3' non-coding sequences encoding transcription termination signals may also be provided. The above mentioned recombinant DNA constructs may also comprise one or more introns in order to facilitate gene expression.

In order to increase the flux through the triterpene pathway, the recombinant DNA constructs capable of directing expression of the serine carboxypeptidase-like acyl transferase, the methyltransferase, or the glucosyltransferase described above may be combined in a transgenic plant.

In addition, a recombinant construct combining the genes of the present invention may be constructed in which in addition to a coding region that is operably linked to a promoter capable of directing expression of a first enzyme of the triterpene pathway, the recombinant construct also contains at least one more coding region operably linked to a promoter capable of directing expression of at least a second enzyme of the current invention. Examples of combinations of the genes of the present invention isolated from *Avena strigosa* are expected to include but not limited to: AsSCPL1+AsMT1; AsSCPL1+AsGT2; AsGT2+AsMT1 and AsSCPL1+AsMT1+AsGT2.

An increased flux through the pathway may also be obtained by combining the recombinant constructs described above in a transgenic plant with constructs encoding the enzymes of the first two steps in the pathway, the oxidosqualene cyclase β-amyrin synthase (the product of the Sad1 gene; Haralampidis K. et al., 2001, *Proc. Natl. Acad. Sci. U.S.A.* 98:13431-13436) and/or the cytochrome P450 enzyme CYP51H10 (encoded by the Sad2 gene; Qi X. et al., 2006, *Proc. Natl. Acad. Sci. U.S.A.* 103:18848-18853). Constructs for overexpression of these two genes have been previously described (Osbourn et al. Mar. 6, 2007 U.S. Pat. No. 7,186,884 B2; Osbourn et al. US 2006-0112448 A1).

Furthermore, a recombinant construct combining the genes of the present invention may be constructed in which in addition to a coding region that is operably linked to a promoter capable of directing expression of a first enzyme of the triterpene pathway, the recombinant construct also contains at least one more coding region operably linked to a promoter capable of directing expression of at least a second enzyme of the triterpene pathway. Examples of combinations of the genes of the present invention isolated from *Avena strigosa* and other genes from the triterpene pathway are expected to include but not limited to:
AsSCPL1+Sad1; AsMT1+Sad1; AsGT2+Sad1; AsSCPL1+Sad2; AsMT1+Sad2; AsGT2+Sad2; AsSCPL1+AsMT1; AsSCPL1+AsGT2; AsGT2+AsMT1; AsSCPL1+AsMT1+AsGT2; AsSCPL1+AsMT1+AsGT2+Sad1; AsSCPL1+AsMT1+AsGT2+Sad2; AsSCPL1+Sad1+Sad2; AsMT1+Sad1+Sad2; AsGT2+Sad1+Sad2; AsSCPL1+AsMT1+Sad1+Sad2; AsSCPL1+AsGT2+Sad1+Sad2; AsMT1+AsGT2+Sad1+Sad2; AsSCPL1+AsMT1+AsGT2+Sad1+Sad2;
AsSCPL1+AsMT1+Sad1; AsSCPL1+AsGT2+Sad1; AsGT2+AsMT1+Sad1; AsSCPL1+AsMT1+Sad2; AsSCPL1+AsGT2+Sad2; and, AsGT2+AsMT1+Sad2;

It may also be desirable to reduce or eliminate expression of the serine carboxypeptidase-like acyl transferase, the methyltransferase, or the a glucosyltransferase of the present invention in plants for some applications. Suppression of the polynucleotides of the invention may result in plants producing lower saponins, which in turn may improve the flavor. In order to accomplish this, a recombinant DNA construct designed for co-suppression of such enzymes can be constructed by linking a polynucleotide encoding the serine carboxypeptidase-like acyl transferase, the methyltransferase, or the glucosyltransferase of the present invention to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated. Construction of chimeric nucleic acid fragments that result in the formation of hair-loop structures where portions of the polynucleotides of the invention are either the stem or the loop or the structure may also be prepared. It may also be possible to use at least a portion of the nucleotide sequence encoding the serine carboxypeptidase-like acyl transferase, the methyltransferase, or the glucosyltransferase of the present invention to prepare constructs that would serve as RNAi to suppress its expression. Any of the recombinant DNA constructs mentioned above may be introduced into a cell to eliminate expression of the serine carboxypeptidase-like acyl transferase, the methyltransferase, or the glucosyltransferase of the present invention in plants. Furthermore, such constructs could be combined with recombinant constructs containing fragments of oxidosqualene cyclase, β-amyrin synthase (the product of the Sad1 gene; (Haralampidis K. et al., 2001, *Proc. Natl. Acad. Sci. U.S.A.* 98:13431-13436) and/or the cytochrome P450 enzyme CYP51H10 (encoded by the Sad2 gene; Qi X. et al., 2006, *Proc. Natl. Acad. Sci. U.S.A.* 103:18848-18853) in order to suppress all steps in the pathway. Examples of combinations of the genes of the present invention isolated from *Avena strigosa* and other genes from the triterpene pathway that may be combined to alter or decrease levels of triterpene saponins are expected to include but not limited to:
AsSCPL1+Sad1; AsMT1+Sad1; AsGT2+Sad1; AsSCPL1+Sad2; AsMT1+Sad2; AsGT2+Sad2; AsSCPL1+AsMT1; AsSCPL1+AsGT2; AsGT2+AsMT1; AsSCPL1+AsMT1+AsGT2; AsSCPL1+AsMT1+AsGT2+Sad1; AsSCPL1+AsMT1+AsGT2+Sad2; AsSCPL1+Sad1+Sad2; AsMT1+Sad1+Sad2; AsGT2+Sad1+Sad2; AsSCPL1+AsMT1+Sad1+Sad2; AsSCPL1+AsGT2+Sad1+Sad2; AsMT1+AsGT2+Sad1+Sad2; AsSCPL1+AsMT1+AsGT2+Sad1+Sad2;
AsSCPL1+AsMT1+Sad1; AsSCPL1+AsGT2+Sad1; AsGT2+AsMT1+Sad1; AsSCPL1+AsMT1+Sad2; AsSCPL1+AsGT2+Sad2; and, AsGT2+AsMT1+Sad2;

In certain embodiments the nucleic acid sequences of the embodiments can be stacked with any combination of polynucleotide sequences of interest, which may be transgenic or non-transgenic, in order to create plants with a desired phenotype. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxin proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792, 931); avirulence and disease resistance genes (Jones et al. (1994) *Science* 266:789; Martin et al. (1993) *Science* 262: 1432; Mindrinos et al. (1994) *Cell* 78:1089); acetolactate synthase (ALS) mutants that lead to herbicide resistance such as the S4 and/or Hra mutations (Lee et al., (1988) EMBO J. 7(5):1241-1248), resistance to inhibitors of glutamine synthase such as phosphinothricin or basta (e.g., bar gene; De Block et al. (1987) EMBO J. 6:2513-2518); HPPD genes that confer tolerance to HPPD inhibiting herbicides such as mesotrione or isoxaflutole (Matringe et al. (2005) Pest Management Science 61:269-276; Dufourmantel et al., (2007) Plant Biotech. J. 5:118-133; see also WO1997049816), genes for tolerance to PPO inhibiting herbicides (Li and Nicholl (2005) Pest Management Science 61:277-285); synthetic auxin resistance genes (US patent application 2005/014737 and Herman et al., (2005) J. Biol. Chem. 280: 24759-24767), and glyphosate resistance (epsps genes, gat genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, yield improvement, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The embodiments of the present invention may be effective against a variety of plant fungal pathogens. Recombinant construct resulting in an increased level of triterpene saponins describe above may be used to produce plants resistant to at least one fungus. Some specific fungal pathogens for the major crops include, but are not limited to, the following: Soybeans: *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Colletotrichum dematium* (*Colletotichum truncatum*), *Corynespora cassiicola, Septoria glycines, Phyllosticta sojicola, Alternaria alternata, Microsphaera diffusa, Fusarium semitectum, Phialophora gregata, Glomerella glycines, Phakopsora pachyrhizi, Fusarium solani*; Canola: *Alternaria brassicae, Leptosphaeria maculans, Rhizoctonia solani, Sclerotinia sclerotiorum, Mycosphaerella brassicicola, Fusarium roseum, Alternaria alternata*; Alfalfa: *Phoma medicaginis* var. *medicaginis, Cercospora medicaginis, Pseudopeziza medicaginis, Leptotrichila medicaginis, Fusarium oxysporum, Verticillium albo-atrum, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrichila medicaginis*; Wheat: *Urocystis agropyri, Alternaria alternata, Cladosporium herbarum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Bipolaris sorokiniana, Claviceps purpurea, Tilletia tritici, Tilletia laevis, Ustilago tritici, Tilletia indica, Rhizoctonia solani*; Sunflower: *Plasmophora halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Cephalosporium acremonium*; Corn: *Colletotrichum graminicola* (*Glomerella graminicola*), *Stenocarpella maydi* (*Diplodia maydis*), *Fusarium moniliforme* var. *subglutinans, Fusarium verticillioides, Gibberella zeae* (*Fusarium graminearum*), *Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellaturn, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Trichoderma viride, Claviceps sorghi, Diplodia macrospora, Sclerophthora macrospora, Sphacelotheca reiliana, Physopella zeae, Cephalosporium maydis, Cephalosporium acremonium*; Sorghum: *Exserohilum turcicum, Cercospora sorghi, Gloeocercospora sorghi, Ascochyta sorghina, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Ramulispora sorghi, Ramulispora sorghicola, Phyllachara sacchari, Sporisorium reilianum* (*Sphacelotheca reiliana*), *Sphacelotheca cruenta, Sporisorium sorghi, Claviceps sorghi, Rhizoctonia solani, Acremonium strictum, Colletotrichum* (*Glomerella*) *graminicola* (*C. sublineolum*), *Fusarium graminearum, Fusarium oxysporum*; and the like.

A variety of nucleic acid amplification-based methods of genetic and physical mapping may be carried out using the instant nucleic acid sequences. Examples include, and are not limited to, allele-specific amplification (Kazazian, H. H. jr, 1989, *J. Lab. Clin. Med.* 11:95-96), polymorphism of PCR-amplified fragments (CAPS; Sheffield, V. C., et al., 1993, *Genomics* 16:325-332), allele-specific ligation (Landegren, U., et al., 1988, *Science* 241:1077-1080), nucleotide extension reactions (Sokolov, B. P., 1990, *Nucleic Acid Res.*

18:3671), radiation hybrid mapping (Walter, M. A. et al., 1994, *Nat. Genet.* 7:22-28), fluorescence in situ hybridization (FISH; Svitashev, S. K. and Somers, D. A., 2002, *Plant Cell Tissue Organ Cult.* 69:205-214), and Happy Mapping (Dear, P. H. and Cook, P. R., 1989, *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for all mapping methods.

While not intending to be bound by any theory or theories of operation, it is believed by those of skill in the art that altered levels of triterpenes have different effects. Increased levels of triterpenes such as avenacin in parts of the plant normally susceptible to fungal pathogen infection may endow the plant with resistance to at least some such pathogens, protecting the plants and so enhancing yield in circumstances of fungal pressure. Foods originating from plants having an increased level of triterpenes are thought to have a cholesterol lowering effect while decreased triterpenes are believed to result in better tasting foods. Accordingly, plants grown with altered levels of AsSCPL1, AsMT1 and/or AsGT2 may contribute to nutritious and/or better-flavored foods. Thus, also included in the invention are the grains from the transgenic plants of the invention.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

General Methods

Standard recombinant DNA and molecular cloning techniques used in the Examples are well known in the art and are described by: (1) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); (2) T. J. Silhavy, M. L. Bennan, and L. W. Enquist, Experiments with Gene Fusions; Cold Spring Harbor Laboratory: Cold Spring Harbor, N.Y. (1984); and (3) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNA Star, Inc.).

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "pmole" mean micromole(s), "g" means gram(s), "μg" means microgram(s), "ng" means nanogram(s), "U" means unit(s), "bp" means base pair(s) and "kB" means kilobase(s).

Example 1

Isolation of Genomic and cDNA Fragments for the Serine Carboxypeptidase-Like Protein (AsSCPL1), the Methyltransferase (AsMT1) and the Glucosyltransferase (AsGT2)

The genomic polynucleotide fragment encoding the genes affected in the serine carboxypeptidase-like protein (AsSCPL1), the methyltransferase (AsMT1) and the glucosyltransferase (AsGT2) was isolated from a BAC library derived from *Avena strigosa* accession S75 genomic DNA and a cDNA library prepared from oat as follows.

A BAC library was constructed from *A. strigosa* accession S75 genomic DNA ((Qi X. et al., 2006, *Proc. Natl. Acad. Sci. U.S.A* 103:18848-18853). DNA probes derived from Sad1 (Osbourn et al. Mar. 6, 2007, U.S. Pat. No. 7,186,884 B2) and Sad2 (Osbourn et al. US 2006-0112448 A1) were used to screen the entire BAC library. A BAC contig spanning a gene cluster for avenacin biosynthesis (Qi X. et al., 2004, *Proc. Natl. Acad. Sci. U.S.A.* 101:8233-8238) was built. BAC finger printing and BAC end sequence analysis allowed us to assemble a contig consisting of BAC clones 462F14, 460D15 and 409O10. Clone 460D15 contains Sad1 and Sad2 (Qi X. et al., 2006, *Proc. Natl. Acad. Sci. U.S.A* 103:18848-18853); Clone 462F14 has about 70 kb overlap with 460D15 at side nearest Sad2 while clone 409O10 overlaps with clone 460D15 by about 35 kb at the side nearest Sad1. Using the end sequence of 409O10 as probe, another BAC clone 341P21 was identified. BAC fingerprinting and PCR analysis confirmed that the other end of clone 409O10 overlaps about 40 kb with clone 341P21. The entire contig is estimated to be 365 kb in length.

Isolation of oat root mRNA and construction of a corresponding cDNA library were described as in Haralampidis K. et al., 2001, *Proc. Natl. Acad. Sci. U.S.A.* 98:13431-13436. The cDNA inserts were cloned into the pGADT7 vector (ClonTech Lab, Inc.) at the Eco RI/Xho I position. A total of 36,864 clones were stored in 96 384-well micro plates. The entire oat root cDNA library was gridded onto two filters for hybridization. The insert DNAs from BAC clones 409O10 and 341P21 were isolated by digestion with Not I, and used as probes to screen the cDNA library. A total of 60 positive clones was identified and the inserts of these clones were sequenced. Sequencing was carried out using the ABI PRISM® Big-Dye™ Terminator Cycle Sequencing Ready Reaction Kit (Applied Biosystems). cDNA sequences were obtained from 52 clones. Apart from 5 unique sequences, the remaining 47 cDNA inserts were grouped into four gene classes. Further analysis enabled the identification of the longest cDNA clones and subsequently the full-length cDNA for each of the four groups.

The first group represented the cDNA of Sad1, so confirming that the BAC contig does indeed span the gene cluster containing this gene.

The full-length cDNA from the second group is predicted to encode a serine carboxypeptidase-like protein AsSCPL1. The nucleotide sequence of this gene is shown in SEQ ID No: 1. The deduced amino acid sequence of nucleotides 56 through 1534 of SEQ ID NO:1 is shown in SEQ ID NO: 2. Nucleotides 1535-1537 represent a stop codon.

The third group of cDNA sequence corresponded to a predicted methyltransferase, AsMT1. The nucleotide sequence of this gene is shown in SEQ ID No: 3. The deduced amino acid sequence of nucleotides 13 through 1074 of SEQ ID NO: 3 is shown in SEQ ID NO: 4. Nucleotides 1075-1077 represent a stop codon.

The fourth group of cDNA sequences correspond to a predicted family 1 glucosyltransferase, AsGT2. The full-length cDNA was obtained by sequence analysis of the oat root putative glucosyltransferase ESTs (ref Sad1 patent). The nucleotide sequence of this gene is shown in SEQ ID No: 5. The deduced amino acid sequence of nucleotides 66 through 1457 of SEQ ID NO:5 is shown in SEQ ID NO: 6. Nucleotides 1458-1460 represent a stop codon.

Figure 2:
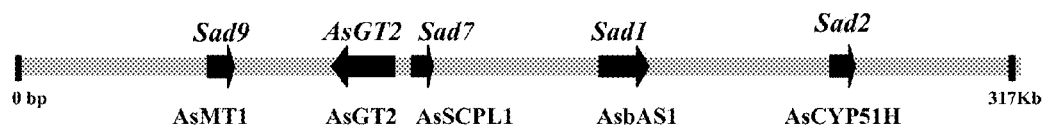
FIG. 2 depicts a 317 kb genomic DNA sequence containing genes for five predicted biosynthetic enzymes (R-amyrin synthase (Sad1), cytochrome P450 CYP51H10 (Sad2), the serine carboxypeptidase-like protein AsSCPL1, the methyltransferase AsMT1 and the glucosyltransferase AsGT2 from *Avena strigosa*.

To obtain genomic sequences of above genes, sequencing of BAC clones 462F14, 460D15, 409O10 and 341P21 from the contig was carried out by standard BAC shotgun sequencing. A BAC contig of about 317 kb was obtained containing genes for five predicted biosynthetic enzymes (beta-amyrin synthase (Sad1), cytochrome P450 CYP51H10 (Sad2), the serine carboxypeptidase-like protein AsSCPL1, the methyltransferase AsMT1 and the glucosyltransferase AsGT2) (FIG. 2). Extensive sequence annotation did not uncover further open reading frames. Northern blot and RT-PCR analysis indicated that all five genes within the BAC contig are expressed preferentially in the roots (FIG. 3). Since avencins are synthesized and accumulate in the oat roots and Sad1 and Sad2 are expressed preferentially in the roots, the other three genes AsSCPL1, AsMT1 and AsGT2 are also likely to be involved in the biosynthesis of avenacins.

Comparison of the genomic DNA sequences and the cDNA sequences provides the predict promoters and genomics sequences of the three genes for serine carboxypeptidase-like protein (AsSCPL1), methyltransferase (AsMT1) and glucosyltransferase (AsGT2). The genomic polynucleotide fragment encoding AsSCPL1, AsMT1 and AsGT2 and the predicted 3-kb promoter sequences are shown in SEQ ID No: 7, SEQ ID No: 8 and SEQ ID No: 9, respectively.

Example 2

Isolation and Characterization of Sad7 Oat Mutants

Seed of the diploid oat species *Avena strigosa* were mutagenized with sodium azide and M2 seed from individual M1 plants were germinated and assessed for root fluorescence as a preliminary screen to identify saponin-deficient, or Sad, oat mutants. Candidate avenacin-deficient mutants were identified on the basis of reduced root fluorescence and confirmed by TLC and HPLC analyses of methanolic root extracts from homozygous M3 seedlings.

Generation of Mutants

Seed of the diploid oat species *Avena strigosa* (accession S75 from the Institute of Grasslands and Environmental Research, Aberystwyth, Wales, UK) was mutagenized with sodium azide essentially as described (Rines, H. W., 1985, *Env. Exp. Bot.*, 25:7-17). Briefly, mutagenesis was performed as follows. Seeds were presoaked in an Erlenmeyer flask sealed with a rubber stopper using 0.5 ml water per seed while shaking in an orbital platform shaker at 120 cycles per minute. After presoaking for 4 hours the water was decanted. A solution of 10 mM sodium azide in 0.1 M sodium phosphate, pH 3.2 was prepared and immediately added to the seeds. After shaking, as above, for 1 hour the mutagen solution was decanted and the seeds rinsed with 5 to 6 changes of water with the last three water rinses extending over a period of 30 minutes. Rinsed seeds were drained and spread over paper in a fume hood to dry. M2 seed from individual M1 plants were germinated and assessed for root fluorescence as indicated below.

The major oat-root saponin avenacin A-1 contains N-methyl anthranilic acid and, thus, is primarily responsible for the bright blue fluorescence of young oat roots (Osbourn A. E. et al., 1994, *Physiol. Mol. Plant Pathol.* 45:457-467). The fact that avenacin A-1 is detectable by UV light allows root fluorescence to be used as a preliminary screen to identify saponin-deficient (Sad) oat mutants. Seed of individual M2 families were germinated and assessed for root fluorescence. In the initial screens ten independent mutants with reduced fluorescence were identified after screening seedlings representing 1,289 M2 families as reported by Papadopoulou K. et al. (1999, *Proc. Natl. Acad. Sci. U.S.A.* 96:12923-1928). Subsequent mutant screens identified a further 82 independent avenacin-deficient mutants isolated on the basis of reduced root fluorescence.

Biochemical Characterization

Analysis of the root extracts of the original ten mutants was carried out as described (Papadopoulou K. et al., 1999, *Proc. Natl. Acad. Sci. U.S.A.* 96:12923-1928). Briefly, M3 seeds were germinated on moist filter paper for 2 days and terminal 0.5 cm sections of the roots from 20 seedlings per line were harvested and extracted in methanol. For HPLC analysis crude methanolic root extracts from M3 seedlings were prepared in triplicate and 100 µl aliquots were analyzed directly on a Hichrom Nucleosil 5 C18 reverse phase column (4.5× 250 mm) under isocratic conditions in 75% methanol (flow rate 1 ml/min) with detection at 225 nm. The four avenacins were quantified by comparison of peak areas with those of standards of known concentration. Extracts for TLC analysis were dried down, resuspended in 1 ml water and applied to SepPak C18 reverse phase cartridges (Waters, Milford, Mass.) that had been pre-conditioned with 10 ml of methanol followed by 10 ml distilled water. After elution with 75% methanol samples were dried down, resuspended in 15 µl of 100% methanol, applied to the TLC plates, and separated using chloroform:methanol:water (13:6:1; v:v:v). Avenacins A-1 and B-1 and other fluorescent components were visualized under UV illumination at 302 nm. The TLC plate was then sprayed with p-anisaldehyde/sulphuric acid/acetic acid (1:1:48, v:v:v) and baked at 130° C. for 5 min to detect all four saponins. Root extracts derived from either M3 or F3 seedlings were compared on at least seven occasions with essentially the same outcome.

Genetic Analysis of Sad Mutants

Test crosses were performed between the Sad mutants and the wild type *A. strigosa* to determine if the saponin-deficient phenotype was due to a single mutation. Analysis of F2 generations from intermutant crosses identified at least 4 complementation groups in the initial 10 mutant lines. These loci were designated Sad1 through Sad4 (Papadopoulou K. et al., 1999, *Proc. Natl. Acad. Sci. U.S.A.* 96:12923-1928). Further analysis of the original 10 mutant lines determined 4 additional loci designated Sad5 through Sad8 (Qi X. et al., 2004, *Proc. Natl. Acad. Sci. U.S.A.* 101:8233-8238).

DNA sequence analysis of the 3 new genes implicated in avenacin biosynthesis (AsSCPL1, AsMT1 and AsGT2) was carried out in Sad5, Sad6, Sad7 and Sad8 mutants. A single nucleotide change from C to T causes amino acid change from serine to phenylalanine in AsSCPL1 at the 137$^{th}$ amino acid in mutant #587 (Sad7) and mutant #616 (originally designated as Sad5) and from proline to leucine at the 79$^{th}$ amino acid in #376 (Sad7), respectively (Table 1). A new mutant #19.1 that had undergone a point mutation in AsSCPL1 was also isolated by screening genomic DNA of a further 82 Sad mutants which were identified by extending the screen based on reduced root fluorescence (as described above) and further analysis using the Surveyor Mutation Detection Kit (Transgenomic). The target cDNA was amplified by PCR. The amplicons from two mutant lines were mixed. Heteroduplex formation and the subsequence procedures for mutant detection were performed according to the manufacter's instructions (Transgenomic Cat No. 706025). Mutant #19.1 contains a point mutation that is predicted to give rise to a change from threonine to isoleucine at the 463$^{rd}$ amino acid. No nucleotide change was found in the AsMT1 and AsGT2 genes in Sad5, Sad6, Sad7 or Sad8 mutants. Allelism tests with mutants #19.1, #616 and #376 indicate that all three mutants correspond to a single locus, Sad7. These data demonstrates that mutant #616, which was originally designated as Sad5, corresponds to the locus Sad7. These results clearly show that Sad7 corresponds to the serine carboxypeptidase-like protein AsSCPL1. AsSCPL1 is required for addition of the acyl group (N-methyl anthranilic acid in the case of the fluorescent avenacins A-1 and B-1 and benzoic acid in the case of the nonfluorescent avenacins A-2 and B-2) to the triterpene skeleton of the avenacins.

Example 3

Isolation and Characterization of Sad9 Oat Mutants

The original mutants #616, #825, #376 and #1243 (Papadopoulou et al. 1999. PNAS 96 12923-1928) do not contain any nucleotide changes in AsMT1 and AsGT2 genes. Sequence analysis was extended to the 82 new Sad mutants that were isolated as described in Example 2. Three mutant M3 lines (#195, #961 and #1310) were identified as having point mutations in the AsMT1 gene (Table 2). No mutations were identified in the AsGT2 gene for any of the mutants in the collection. DNA sequence analysis confirmed a single nucleotide change in the coding sequences in the three mutants, #195, #961 and #1310. Each of these nucleotide changes is predicted to cause an amino acid change (Table 2).

Roots of these three mutants lack the bright blue fluorescence associated with avenacin A-1 but fluoresce dull purple fluorescence under UV illumination. These mutants are referred to as "purple mutants". One more purple mutant #841 was identified from the 82 new Sad mutants using TLC-based methods (Table 2). Metabolite analysis of purple mutants was conducted as described below. Ten root tips (0.5 cm in length) from each line were excised and soaked in 500 ul 75% MeOH for between one hour and overnight. Following centrifugation the supernatant was transferred to a new tube, dried down and the extract resuspended in 20 ul 100% MeOH. Ten ul samples were loaded onto a TLC plate and the TLC developed in $CHCl_3$:MeOH:d$H_2O$ (13:6:1 vol/vol/vol). TLC plates were examined under UV illumination. All purple mutants including #841 had a clear purple spot on the TLC plate. Sequence analysis of #841 confirmed a single nucleotide change from C to T in the coding sequence of this mutant. This change is predicted to cause alanine at amino acid 333 to change to valine (see Table 1).

The purple mutants were intercrossed (#195×#1310, #961×#1310, #195×#961) for tests of allelism. The heterozygote was confirmed by sequence analysis of the two mutant alleles in the F1 hybrids. All F1 plants retained the "purple root" phenotype. These results indicate that the three purple mutants are mutant alleles at the same genetic locus, now defined as Sad9. The genetic data, RNA expression data (FIG. 3) and metabolite analysis indicate that Sad9 corresponds to AsMT1, a methyltransferase that is required for avenacin biosynthesis in oats. The function of this methyltransferase is likely to be in methylation of the anthranilic acid group of the fluorescent avenacins, A-1 and B-1.

Example 4

Characterization of the Glucosyltransferase in the Sad Gene Cluster

In the avenacin gene cluster, 4 out of the 5 five genes within the BAC contig spanning the Sad gene cluster have been shown to be directly involved in the avenacin biosynthetic pathway (Osbourn et al. Mar. 6, 2007 U.S. Pat. No. 7,186,884 B2; Osbourn et al. US 2006-0112448 A1 and Examples 2 & 3). However, mutants for AsGT2 were not represented in our extended collection of 92 reduced root fluorescence mutants even though multiple mutant alleles for the other four genes were identified. If AsGT2 is required for addition of one/more sugars to the trisaccharide moiety of avenacins then loss of function of AsGT2 may not result in a reduced root fluorescence phenotype since addition of the fluorescent group (N-methyl anthranilic acid) is unlikely to be affected. Other possibilities are that there is functional redundancy or that mutations in AsGT2 are lethal. Alternatively AsGT2 may catalyse the formation of acyl glucose intermediates that are used for AsSCPL1-mediated acylation. Therefore the function of AsGT2 was demonstrated biochemically.

To test the function of AsGT2, the AsGT2 cDNA was cloned into the Novagen pET-19b expression vector and expressed in *E. coli* as follows *E. coli* cells containing the expression construct were inoculated onto LB agar supplemented with 34 μg/mL chloramphenicol, 50 μg/mL carbenicillin, 2.5 mM betaine and 0.6 M sorbitol. The expression cells were grown overnight at 37 degrees Celsius. For protein expression the cells on solid media were used to inoculate ten 250 mL flasks with 50 mL of liquid media supplemented as above. Cultures were grown to an $OD_{600}$ of approximately 0.6 at 37 degrees Celsius with shaking. The cultures were then transferred to a 16 degree Celsius shaking incubator for 30 minutes before addition of IPTG inducer to 0.1 mM final concentration. Cultures were then incubated overnight at 16 degrees Celsius with shaking.

Induced cells were harvested by centrifugation at 7,000×g for 10 minutes at 4 degree Celsius. The cellular pellet was resuspended in 5-10 mL of lysis-bind buffer (300 mM NaCl, 50 mM sodium phosphate, 20 mM imidazole, 5% glycerol, pH 7.8) with Roche EDTA-free protease inhibitor (1 tablet per 50 mL). Cells were lysed twice using a French press, keeping ice-cold throughout. The lysate was centrifuged at 10,000×g for 45 min at 4 degrees Celsius. The supernatant was filtered using a 0.2 µm syringe-filter prior to injection for FPLC at a rate of 0.5 mL/min.

FPLC was carried out using a prepacked 1 mL HiTrap chelating HP column (Amersham) and the FPLC system. The purification column was charged using 0.1 M $NiCl_2$ following the manufacturers recommendations. The column was pre-equilibrated with lysis-bind buffer prior to sample injection. Following injection the column was washed with lysis-bind buffer for 30 min to 1 hour before a gradient program to Elution buffer B (300 mM NaCl, 50 mM sodium phosphate buffer, 700 mM imidazole, 5% glycerol, pH 8.0).

TABLE 3

Conditions for elution of protein from the HiTrap chelating HP column.

| Time (min) | % B | ml/min |
|---|---|---|
| 0 | 8 | 1.0 |
| 20 | 10 | 1.0 |
| 40 | 100 | 1.0 |
| 50 | 100 | 1.0 |

Elution fractions of 1 mL were collected on ice and 20 µl used to visualize results on a 10% PAGE system. Fractions of interest were pooled and dialyzed overnight at 4 degrees Celsius against 50 mM sodium phosphate buffer pH 7.5 with 50% glycerol and 2 mM $MgCl_2$. Aliquots were snap frozen in liquid nitrogen and stored at −80 degrees Celsius.

Radioactive assays with a complex acceptor substrate were used to detect low level activity with pure or enriched substrates. The assays contained 4 µl $^{14}$C-UDP-glucose, 25 µl 50 mM potassium phosphate buffer pH 7.6, 0.25 µl 100 mM acceptor substrate in DMSO, 5 µl of the dialyzed protein preparation, and 3 µl 10 mM DTT. The reaction proceeded at 28 degrees Celsius for 2.5 hours shaking gently before stopping by the addition of 50 µl chloroform:methanol (2:1). The aqueous phase was extracted three more times with chloroform methanol and the solvent phases were pooled. The extracts were dried down at 60 degrees Celsius and resuspended in 40 µl of chloroform:methanol. The aqueous phase was dried down also and resuspended in water. A silica-gel TLC plate was loaded with 15 µl of the extracts and chromatographed with chloroform:methanol:water (13:6:1) against standards.

The acceptor substrates tested were β-amyrin-arabinoside, benzoic acid and salicylic acid. The sugars donors tested were D-glucose and L-arabinose.

To confirm the chemical structures of the products visualized by the radioactive assay a non-radioactive LC-MS assay was developed. This assay comprised 10 µl 20 mM UDP-glucose or UDP-arabinose, 60 µl 50 mM potassium phosphate pH 7.6, 2 µl 1 M $MgCl_2$, 4 µl 100 mM acceptor substrates in DMSO (or 8 µl synthetic substrate, DMSO only for the controls), 20 µl protein preparation, 10 µl 100 mM DTT. The reactions were incubated at 28 degrees with gentle shaking for 3.5 hours. Reactions were stopped by the addition of 100% methanol, which was then evaporated from the reaction at 50 degrees Celsius, and were analysed by LC/MS/MS using reversed-phase chromatography. Samples (10 µl) were run on a 100×2 mm 3µ Luna C18(2) column (Phenomenex) at 250 µL·$min^{-1}$, 30° C., in the following gradient of methanol+ 0.1% formic acid versus water+0.1% formic acid:

TABLE 4

Methanol gradient used for reverse phase chromatography.

| time (min) | % MeOH |
|---|---|
| 0 | 10 |
| 40 | 95 |
| 41 | 10 |
| 48 | 10 |

Detection was by UV (214 nm, band-width 9 nm, and spectra from 200-600 nm) and electrospray MS, in either positive or negative mode in separate runs. Spray chamber conditions were 50 units sheath gas, no aux/sweep, 5.2 kV spray voltage in positive, 5.0 kV in negative mode, 325° C. capillary temperature. A second scan event of data dependent $MS^2$ was carried out by trapping at an isolation width of 5.0 amu and fragmenting at 35% collision energy.

Results were as shown in Table 4. A "+" denotes activity.

TABLE 5

Activity of AsGT2 towards benzoid acid and salicylate substrates.

| | Benzoic acid | | Salicylate | |
|---|---|---|---|---|
| | L-Ara | D-Glu | L-Ara | D-Glu |
| AsGT2 | +++ | +++ | + | +++ |

Assays of activity of AsGT2 towards J3-amyrin-arabinoside were inconclusive due to technical problems with chromatography and detection. However, the results with benzoic acid and salicylate clearly demonstrate that AsGT2 functions as a glucosyl transferase on substrates with ring structures similar to β-amyrin. Combined with the fact that, like the other enzymes in the pathway, AsGT2 is expressed only in roots and that the gene is located within the avenacin biosynthetic gene cluster, these results indicate that this gene encodes a glucosyl transferase that is required for avenacin synthesis.

Example 5

Recombinant DNA Constructs to Express AsSCPL1 in Other Species

Following are examples of recombinant DNA constructs that can be used to express AsSCPL1 in monocot or dicot species, using corn and soybean as examples. Constitutive promoters are used, and a person skilled in the art will appreciate that, depending on the target pathogen or other considerations, targeted promoters such as those of the examples described earlier in this text may be equally or even more efficacious or preferable due to special end uses of the plant material. Depending on the species and the enzymatic activities present in that species, other genes from the biosynthetic pathways might be included to increase expression levels.

In the examples below the following abbreviations for nucleic acid fragments comprising the different components are used:

"RB" and "LB" correspond to the right and left borders of the T-DNA.

"CAMV35S ENH" is the enhancer region of the cauliflower mosaic virus 35S promoter, which increases the level of expression of promoters to which it is attached (Benfey P. N., et al., 1990, EMBO J. 9:1685-1696).

"UBI PRO" is the promoter of the maize ubiquitin gene, as described in (Christensen et al., 1992, Plant Mol. Biol. 18:675-689).

"UBI 5'UTR" is the 5' leader region of the same maize ubiquitin gene.

"UBI INTRON1" is the intron of the same ubiquitin gene. Inclusion of this intron has been shown to increase expression levels.

"ATTR1" is a recombination site as described in the Gateway™ cloning system manual (Invitrogen, Carlsbad, Calif., USA).

"CCDB" is a bacterial negative selectable marker described in the Gateway™ cloning system manual.

"ATTR2" is a recombination site as described in the Gateway™ cloning system manual.

"PINII" is the transcription termination gene from the potato protease inhibitor II gene.

"CAMV35SPRO" is the promoter of the cauliflower mosaic virus 35S gene, a constitutive promoter commonly used in plants (Odell J. T. et al., 1985, Nature 313:810-812).

"ADH1 INTRON1" is the intron of the maize ADH1 gene. Inclusion of this intron has been shown to increase expression levels (Luehrsen K. R. and Walbot V., 1991, *Mol. Gen. Genet.* 225:81-93).

"BAR" is an herbicide resistance gene commonly used as a selectable marker in corn transformation.

"SCP1" is a synthetic constitutive promoter for use in plants and is described in U.S. Pat. No. 6,072,050.

"OMEGA 5' UTR" is the 5' leader region of a tobacco mosaic virus gene, whose use has been shown to enhance translation levels (Gallie et al., 1989, in *Molecular Biology of RNA*, ed. Cech (Liss, New York), pp. 237-256).

"SPC1" is a coding sequence for a polypeptide that provides resistance to the antibiotic spectinomycin, allowing bacterial selection Svab, Z. and Maliga, P., 1991, *Mol. Gen. Genet.* 228:316-319.

"ColE1 ORI" is a DNA origin of replication functional in *E. coli*.

Constructs for the Expression of Saponin Biosynthetic Genes in Maize

A fragment containing the open reading frame of AsSCPL1 is obtained respectively from clones described in example 1. PCR amplification is carried out with primers that result in the open reading frames being flanked by unique restriction sites allowing their directional cloning into these unique restriction sites of modified Gateway™ Entry Vectors (Invitrogen, Carlsbad, Calif., USA). After ligation of the fragment into the Gateway™ Entry Vector, the "entry vector" consists of ATTL1-AsSCPL1-ATTL2, and contains kanamycin resistance for bacterial selection. ATTL1 and ATTL2 are recombination sites provided in the Invitrogen Gateway™ cloning system (Carlsbad, Calif., USA).

Maize Recombinant DNA Construct 1: E35S-UBI-AsSCPL1-PINII

This construct can be used to express the AsSCPL1 gene alone in corn. The AsSCPL1 entry vector is used in a Gateway™ LR reaction with a Gateway™ modified *Agrobacterium* transformation vector backbone modified from pSB1 (Komari, T. et al., 1996, Plant J. 10:165-174) by the addition of the following components at the cos site: RB-CAMV35S ENH-UBI PRO-UBI 5'UTR-UBI INTRON1-ATTR1-CCDB-ATTR2-PINII+CAMV35S ENH-CAMV35S PRO-ADH1 INTRON1-BAR-PINII-LB-SPC-ColE1 ORI. In this Gateway™ reaction, ATTL1 and ATTL2 recombine with ATTR1 and ATTR2, thereby transferring the AsSCPL1 gene into the destination vector, replacing CCDB, which is toxic to *E. coli*, and allowing screening for successful clones as described in the Gateway™ manual (Invitrogen, Carlsbad, Calif., USA). This resulting construct contains a T-DNA which will be transferred into the plant genome and contains RB-CAMV35S ENH-UBI PRO-UBI 5'UTR-UBI INTRON1-ATTB1-AsSCPL1-ATTB2-PINII+CAMV35S ENH-CAMV35S PRO-ADH1 INTRON1-BAR-PINII-LB. The nucleotide sequence outside of the region between the RB and LB is described in Kormai, T. et al., op cit., with the exception of the SPC and ColE1 components. This construct is electroporated into LBA4404 *Agrobacterium tumefaciens* cells and used in transformation experiments such as those described in Example 8 below.

Constructs for the Expression of Saponin Biosynthetic Genes in Soybean

The AsSCPL1 open reading frame is obtained by PCR amplification as described above for the maize construct.

Soybean Recombinant DNA Construct 1: SCP1-O'-AsSCPL1-PINII

This construct can be used to express the AsSCPL1 gene alone in dicots. After ligating a polynucleotide comprising the open reading frame of AsSCPL1 into a vector containing SCP1 PRO-OMEGA 5' UTR-same unique restriction sites as those flanking AsSCPL1-PINII, the plasmid is linearized for bombardment and extracting the desired band of DNA from a gel. This process also removes the nucleotides encoding ampicillin resistance used for bacterial selection. This fragment contains SCP1 PRO-OMEGA 5'UTR-AsSCPL1-PINII and is used for soybean transformation as described in Example 9 below.

Example 6

Recombinant DNA Constructs to Express AsMT1 in Other Species

Following are examples of recombinant DNA constructs that can be used to express AsMT1 in monocot or dicot species, using corn and soybean as examples. Constitutive promoters are used, and a person skilled in the art will appreciate that, depending on the target pathogen or other considerations, targeted promoters such as those of the examples described earlier in this text may be equally or even more efficacious or preferable due to special end uses of the plant material. Depending on the species and the enzymatic activities present in that species, other genes from the biosynthetic pathways might be included to increase expression levels.

In the examples below the following abbreviations for nucleic acid fragments comprising the different components are used:

"RB" and "LB" correspond to the right and left borders of the T-DNA.

"CAMV35S ENH" is the enhancer region of the cauliflower mosaic virus 35S promoter, which increases the level of expression of promoters to which it is attached (Benfey P. N., et al., 1990, EMBO J. 9:1685-1696).

"UBI PRO" is the promoter of the maize ubiquitin gene, as described in (Christensen et al., 1992, Plant Mol. Biol. 18:675-689).

"UBI 5'UTR" is the 5' leader region of the same maize ubiquitin gene.

"UBI INTRON1" is the intron of the same ubiquitin gene. Inclusion of this intron has been shown to increase expression levels.

"ATTR1" is a recombination site as described in the Gateway™ cloning system manual (Invitrogen, Carlsbad, Calif., USA).

"CCDB" is a bacterial negative selectable marker described in the Gateway™ cloning system manual.

"ATTR2" is a recombination site as described in the Gateway™ cloning system manual.

"PINII" is the transcription termination gene from the potato protease inhibitor II gene.

"CAMV35SPRO" is the promoter of the cauliflower mosaic virus 35S gene, a constitutive promoter commonly used in plants (Odell J. T. et al., 1985, *Nature* 313:810-812).

"ADH1 INTRON1" is the intron of the maize ADH1 gene. Inclusion of this intron has been shown to increase expression levels (Luehrsen K. R. and Walbot V., 1991, *Mol. Gen. Genet.* 225:81-93).

"BAR" is an herbicide resistance gene commonly used as a selectable marker in corn transformation.

"SCP1" is a synthetic constitutive promoter for use in plants and is described in U.S. Pat. No. 6,072,050.

"OMEGA 5' UTR" is the 5' leader region of a tobacco mosaic virus gene, whose use has been shown to enhance translation levels (Gallie et al., 1989, in *Molecular Biology of RNA*, ed. Cech (Liss, New York), pp. 237-256).

"SPC1" is a coding sequence for a polypeptide that provides resistance to the antibiotic spectinomycin, allowing bacterial selection Svab, Z. and Maliga, P., 1991, *Mol. Gen. Genet.* 228:316-319.

"ColE1 ORI" is a DNA origin of replication functional in *E. coli*.

Constructs for the Expression of Saponin Biosynthetic Genes in Maize

A fragment containing the open reading frame of AsMT1 is obtained respectively from clones described in example 1. PCR amplification is carried out with primers that result in the open reading frames being flanked by unique restriction sites allowing their directional cloning into these unique restriction sites of modified Gateway™ Entry Vectors (Invitrogen, Carlsbad, Calif., USA). After ligation of the fragment into the Gateway™ Entry Vector, the "entry vector" consists of ATTL1-AsMT1-ATTL2, and contains kanamycin resistance for bacterial selection. ATTL1 and ATTL2 are recombination sites provided in the Invitrogen Gateway™ cloning system (Carlsbad, Calif., USA).

Maize Recombinant DNA Construct 1: E35S-UBI-AsMT1-PINII

This construct can be used to express the AsMT1 gene alone in corn. The AsMT1 entry vector is used in a Gateway™ LR reaction with a Gateway™ modified *Agrobacterium* transformation vector backbone modified from pSB1 (Komari, T. et al., 1996, Plant J. 10:165-174) by the addition of the following components at the cos site: RB-CAMV35S ENH-UBI PRO-UBI 5'UTR-UBI INTRON1-ATTR1-CCDB-ATTR2-PINII+CAMV35S ENH-CAMV35S PRO-ADH1 INTRON1-BAR-PINII-LB-SPC-ColE1 ORI. In this Gateway™ reaction, ATTL1 and ATTL2 recombine with ATTR1 and ATTR2, thereby transferring the AsMT1 gene into the destination vector, replacing CCDB, which is toxic to *E. coli*, and allowing screening for successful clones as described in the Gateway™ manual (Invitrogen, Carlsbad, Calif., USA). This resulting construct contains a T-DNA which will be transferred into the plant genome and contains RB-CAMV35S ENH-UBI PRO-UBI 5'UTR-UBI INTRON1-ATTB1-AsMT1-ATTB2-PINII+CAMV35S ENH-CAMV35S PRO-ADH1 INTRON1-BAR-PINII-LB. The nucleotide sequence outside of the region between the RB and LB is described in Kormai, T. et al., op cit., with the exception of the SPC and ColE1 components. This construct is electroporated into LBA4404 *Agrobacterium tumefaciens* cells and used in transformation experiments such as those described in Example 8 below.

Constructs for the Expression of Saponin Biosynthetic Genes in Soybean

The AsMT1 open reading frame is obtained by PCR amplification as described above for the maize construct.

Soybean Recombinant DNA Construct 1: SCP1-O'-AsMT1-PINII

This construct can be used to express the AsMT1 gene alone in dicots. After ligating a polynucleotide comprising the open reading frame of AsMT1 into a vector containing SCP1 PRO-OMEGA 5' UTR-same unique restriction sites as those flanking AsMT1-PINII, the plasmid is linearized for bombardment and extracting the desired band of DNA from a gel. This process also removes the nucleotides encoding ampicillin resistance used for bacterial selection. This fragment contains SCP1 PRO-OMEGA 5'UTR-AsMT1-PINII and is used for soybean transformation as described in Example 9 below.

Example 7

Recombinant DNA Constructs to Express AsGS2 in Other Species

Following are examples of recombinant DNA constructs that can be used to express AsGS2 in monocot or dicot species, using corn and soybean as examples. Constitutive promoters are used, and a person skilled in the art will appreciate that, depending on the target pathogen or other considerations, targeted promoters such as those of the examples described earlier in this text may be equally or even more efficacious or preferable due to special end uses of the plant material. Depending on the species and the enzymatic activities present in that species, other genes from the biosynthetic pathways might be included to increase expression levels.

In the examples below the following abbreviations for nucleic acid fragments comprising the different components are used:

"RB" and "LB" correspond to the right and left borders of the T-DNA.

"CAMV35S ENH" is the enhancer region of the cauliflower mosaic virus 35S promoter, which increases the level of expression of promoters to which it is attached (Benfey P. N., et al., 1990, EMBO J. 9:1685-1696).

"UBI PRO" is the promoter of the maize ubiquitin gene, as described in (Christensen et al., 1992, *Plant Mol. Biol.* 18:675-689).

"UBI 5'UTR" is the 5' leader region of the same maize ubiquitin gene.

"UBI INTRON1" is the intron of the same ubiquitin gene. Inclusion of this intron has been shown to increase expression levels.

"ATTR1" is a recombination site as described in the Gateway™ cloning system manual (Invitrogen, Carlsbad, Calif., USA).

"CCDB" is a bacterial negative selectable marker described in the Gateway™ cloning system manual.

"ATTR2" is a recombination site as described in the Gateway™ cloning system manual.

"PINII" is the transcription termination gene from the potato protease inhibitor II gene.

"CAMV35SPRO" is the promoter of the cauliflower mosaic virus 35S gene, a constitutive promoter commonly used in plants (Odell J. T. et al., 1985, *Nature* 313:810-812).

"ADH1 INTRON1" is the intron of the maize ADH1 gene. Inclusion of this intron has been shown to increase expression levels (Luehrsen K. R. and Walbot V., 1991, *Mol. Gen. Genet.* 225:81-93).

"BAR" is an herbicide resistance gene commonly used as a selectable marker in corn transformation.

"SCP1" is a synthetic constitutive promoter for use in plants and is described in U.S. Pat. No. 6,072,050.

"OMEGA 5' UTR" is the 5' leader region of a tobacco mosaic virus gene, whose use has been shown to enhance translation levels (Gallie et al., 1989, in *Molecular Biology of RNA*, ed. Cech (Liss, New York), pp. 237-256).

"SPC1" is a coding sequence for a polypeptide that provides resistance to the antibiotic spectinomycin, allowing bacterial selection Svab, Z. and Maliga, P., 1991, *Mol. Gen. Genet.* 228:316-319.

"ColE1 ORI" is a DNA origin of replication functional in *E. coli*.

Constructs for the Expression of Saponin Biosynthetic Genes in Maize

A fragment containing the open reading frame of AsGS2 is obtained respectively from clones described in example 1. PCR amplification is carried out with primers that result in the open reading frames being flanked by unique restriction sites allowing their directional cloning into these unique restriction sites of modified Gateway™ Entry Vectors (Invitrogen, Carlsbad, Calif., USA). After ligation of the fragment into the Gateway™ Entry Vector, the "entry vector" consists of ATTL1-AsGS2-ATTL2, and contains kanamycin resistance for bacterial selection. ATTL1 and ATTL2 are recombination sites provided in the Invitrogen Gateway™ cloning system (Carlsbad, Calif., USA).

Maize Recombinant DNA Construct 1: E35S-UBI-AsGS2-PINII

This construct can be used to express the AsGS2 gene alone in corn. The AsGS2 entry vector is used in a Gateway™ LR reaction with a Gateway™ modified *Agrobacterium* transformation vector backbone modified from pSB1 (Komari, T. et al., 1996, *Plant J.* 10:165-174) by the addition of the following components at the cos site: RB-CAMV35S ENH-UBI PRO-UBI 5'UTR-UBI INTRON1-ATTR1-CCDB-ATTR2-PINII+CAMV35S ENH-CAMV35S PRO-ADH1 INTRON1-BAR-PINII-LB-SPC-ColE1 ORI. In this Gateway™ reaction, ATTL1 and ATTL2 recombine with ATTR1 and ATTR2, thereby transferring the AsGS2 gene into the destination vector, replacing CCDB, which is toxic to *E. coli*, and allowing screening for successful clones as described in the Gateway™ manual (Invitrogen, Carlsbad, Calif., USA). This resulting construct contains a T-DNA which will be transferred into the plant genome and contains RB-CAMV35S ENH-UBI PRO-UBI 5'UTR-UBI INTRON1-ATTB1-AsGS2-ATTB2-PINII+CAMV35S ENH-CAMV35S PRO-ADH1 INTRON1-BAR-PINII-LB. The nucleotide sequence outside of the region between the RB and LB is described in Kormai, T. et al., op cit., with the exception of the SPC and ColE1 components. This construct is electroporated into LBA4404 *Agrobacterium tumefaciens* cells and used in transformation experiments such as those described in Example 8 below.

Constructs for the Expression of Saponin Biosynthetic Genes in Soybean

The AsGS2 open reading frame is obtained by PCR amplification as described above for the maize construct.

Soybean Recombinant DNA Construct 1: SCP1-O'-AsGS2-PINII

This construct can be used to express the AsGS2 gene alone in dicots. After ligating a polynucleotide comprising the open reading frame of AsGS2 into a vector containing SCP1 PRO-OMEGA 5' UTR-same unique restriction sites as those flanking AsGS2-PINII, the plasmid is linearized for bombardment and extracting the desired band of DNA from a gel. This process also removes the nucleotides encoding ampicillin resistance used for bacterial selection. This fragment contains SCP1 PRO-OMEGA 5'UTR-AsGS2-PINII and is used for soybean transformation as described in Example 9 below.

Example 8

*Agrobacterium*-Mediated Transformation of Maize and Regeneration of Transgenic Plants The recombinant DNA constructs prepared in Examples 5-7 above may be used to prepare transgenic maize plants as follows.

Maize may be transformed with any of the polynucleotide constructs described in Examples 5-7 using the method of Zhao (U.S. Pat. No. 5,981,840, and PCT patent publication WO98/32326). Briefly, immature embryos are isolated from maize and the embryos contacted with a suspension of *Agrobacterium*, where the bacteria are capable of transferring the polynucleotide construct to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The callus is then regenerated into plants (step 5: the regeneration step), and calli grown on selective medium are cultured on solid medium to regenerate the plants.

Example 9

Transformation of Somatic Soybean Embryo Cultures with Soybean Expression Vectors and Regeneration of Soybean Plants The recombinant DNA constructs prepared in Examples 5-7 above may be used to prepare transgenic soybean plants as follows.

Culture Conditions:

Soybean embryogenic suspension cultures (cv. Jack) are maintained in 35 mL liquid medium SB196 (infra) on a rotary shaker, 150 rpm, 26° C. with cool white fluorescent lights on 16:8 h day/night photoperiod at light intensity of 60-85 µE/m2/s. Cultures are subcultured every 7 days to two weeks by inoculating approximately 35 mg of tissue into 35 mL of fresh liquid SB196 (the preferred subculture interval is every 7 days).

Soybean embryogenic suspension cultures are transformed with the soybean expression plasmids by the method of particle gun bombardment (Klein et al., *Nature*, 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants are picked 45-55 days after planting. Seeds are removed from the pods and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and are maintained at 26° C. with cool white fluorescent lights on 16:8 h day/night photoperiod at light intensity of 60-80 µE/m2/s for eight weeks, with a media change after 4 weeks. After incubation on SB1 medium, secondary embryos are cut and placed into SB196 liquid media for 7 days.

Preparation of DNA for Bombardment:

Either an intact plasmid or a DNA plasmid fragment containing the genes of interest and the selectable marker gene are used for bombardment. Fragments from soybean expression plasmids, the construction of which is described herein, are obtained by gel isolation of digested plasmids. In each case, 100 µg of plasmid DNA is used in 0.5 mL of the specific enzyme mix described below. Plasmids are digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 h. The resulting DNA fragments are separated by gel electrophoresis on 1% SeaPlaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 µL aliquot of sterile distilled water containing 3 mg of gold particles (3 mg gold) is added to 30 µL of a 10 ng/µL DNA solution (DNA fragment prepared as described herein), 25 µL 5M $CaCl_2$ and 20 µL of 0.1 M spermidine. The mixture is shaken 3 min on level 3 of a vortex shaker and spun for 10 sec in a bench microfuge. The supernatant is removed, followed by a wash with 400 µL 100% ethanol and another brief centrifugation. The 400 µL ethanol is removed and the pellet is resuspended in 40 µL of 100% ethanol. Five µL of DNA suspension is dispensed to each flying disk of the Biolistic PDS1000/HE instrument disk. Each 5 µL aliquot contains approximately 0.375 mg gold per bombardment (e.g., per disk).

Tissue Preparation and Bombardment with DNA:

Approximately 150-200 mg of seven day old embryogenic suspension cultures is placed in an empty, sterile 60×15 mm petri dish and the dish is covered with plastic mesh. The chamber is evacuated to a vacuum of 27-28 inches of mercury, and tissue is bombarded one or two shots per plate with membrane rupture pressure set at 1100 PSI. Tissue is placed approximately 3.5 inches from the retaining/stopping screen.

Selection of Transformed Embryos:

Transformed embryos are selected using chlorsulfuron (when the acetolactate synthase (ALS) gene is used as the selectable marker).

Following bombardment, the tissue is placed into fresh SB196 media and cultured as described above. Six to eight days post-bombardment, the SB196 is exchanged with fresh SB196 containing 100 ng/mL chlorsulfuron. The selection media is refreshed weekly. Four to six weeks post-selection, green, transformed tissue is observed growing from untransformed, necrotic embryogenic clusters. Isolated, green tissue is removed and inoculated into multiwell plates to generate new, clonally propagated, transformed embryogenic suspension cultures.

Embryo Maturation:

Transformed embryogenic clusters from production transformation are cultured for four-six weeks in multiwell plates as described above at 26° C. in SB196 under cool white fluorescent (Phillips cool white Econowatt F40/CW/RS/EW) and Agro (Phillips F40 Agro) bulbs (40 watt) on a 16:8 h photoperiod with light intensity of 90-120 µE/m$^2$s. After this time embryo clusters are removed to a solid agar media, SB166, for one-two weeks and then subcultured to SB103 medium for 3-4 weeks to mature embryos. After maturation on plates in SB103, individual embryos are removed from the clusters, dried and screened for the desired phenotype. Such phenotype may be, but is not limited to, altered levels of saponin or altered levels of resistance against at least one fungus. When desired, plants are obtained from some events as described below.

Embryo Desiccation and Germination:

Matured individual embryos are desiccated by placing them into an empty, small petri dish (60×15 mm) for approximately four-seven days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then planted in Redi-Earth in a 24-cell pack tray, and covered with a clear plastic dome. After one-two weeks the dome is removed and plants hardened off for a further week. If plantlets look hardy they are transplanted to a 10 inch pot of Redi-Earth with up to 3 plantlets per pot. After ten to sixteen weeks, mature seeds are harvested, chipped and analyzed for the desired phenotype.

Media Recipes:

| SB 196 - FN Lite Liquid Proliferation Medium (per liter) | |
| --- | --- |
| MS FeEDTA - 100× Stock 1 | 10 mL |
| MS Sulfate - 100× Stock 2 | 10 mL |
| FN Lite Halides - 100× Stock 3 | 10 mL |
| FN Lite P, B, Mo - 100× Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

| FN Lite Stock Solutions | | | | |
| --- | --- | --- | --- | --- |
| Stock Number | | | 1000 mL | 500 mL |
| 1 | MS Fe EDTA 100× Stock | | | |
| | $Na_2$ EDTA* | | 3.724 g | 1.862 g |
| | $FeSO_4$—$7H_2O$ | | 2.784 g | 1.392 g |
| 2 | MS Sulfate 100× stock | | | |
| | $MgSO_4$—$7H_2O$ | | 37.0 g | 18.5 g |
| | $MnSO_4$—$H_2O$ | | 1.69 g | 0.845 g |
| | $ZnSO_4$—$7H_2O$ | | 0.86 g | 0.43 g |
| | $CuSO_4$—$5H_2O$ | | 0.0025 g | 0.00125 g |
| 3 | FN Lite Halides 100× Stock | | | |
| | $CaCl_2$—$2H_2O$ | | 30.0 g | 15.0 g |
| | KI | | 0.083 g | 0.0715 g |
| | $CoCl_2$—$6H_2O$ | | 0.0025 g | 0.00125 g |

-continued

| FN Lite Stock Solutions | | | |
|---|---|---|---|
| Stock Number | | 1000 mL | 500 mL |
| 4 | FN Lite P, B, Mo 100× Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g glucose
2 mL 2,4-D (20 mg/L final concentration)
pH 5.7
8 g TC agar

SB199 Solid Medium (Per Liter)

1 package MS salts (Gibco/BRL—Cat. No. 11117-066)
1 mL B5 vitamins 1000× stock
30 g Sucrose
4 ml 2,4-D (40 mg/L final concentration)
pH 7.0
2 gm Gelrite

SB 166 Solid Medium (Per Liter)

1 package MS salts (Gibco/BRL—Cat. No. 11117-066)
1 mL B5 vitamins 1000× stock
60 g maltose
750 mg MgCl$_2$ hexahydrate
5 g activated charcoal
pH 5.7
2 g gelrite

SB 103 Solid Medium (Per Liter)

1 package MS salts (Gibco/BRL—Cat. No. 11117-066)
1 mL B5 vitamins 1000× stock
60 g maltose
750 mg MgCl$_2$ hexahydrate
pH 5.7
2 g gelrite

SB 71-4 Solid Medium (Per Liter)

1 bottle Gamborg's B5 salts w/ sucrose (Gibco/BRL—Cat. No. 21153-036)
pH 5.7
5 g TC agar

2,4-D Stock

Obtain premade from Phytotech Cat. No. D 295—concentration 1 mg/mL

B5 Vitamins Stock (Per 100 mL)

Store aliquots at −20° C.
10 g myo-inositol
100 mg nicotinic acid
100 mg pyridoxine HCl
1 g thiamine If the solution does not dissolve quickly enough, apply a low level of heat via the hot stir plate.

| SB 228 - Soybean Histodifferentiation and Maturation (SHaM) (per liter) | |
|---|---|
| DDI H$_2$O | 600 mL |
| FN-Lite Macro Salts for SHaM 10× | 100 mL |
| MS Micro Salts 1000× | 1 mL |
| MS FeEDTA 100× | 10 mL |
| CaCl 100× | 6.82 mL |
| B5 Vitamins 1000× | 1 mL |
| L-Methionine | 0.149 g |
| Sucrose | 30 g |
| Sorbitol | 30 g |

Adjust volume to 900 mL pH 5.8

Autoclave

Add to cooled media (≤30° C.):

*Glutamine (final concentration 30 mM) 4% 110 mL

*Note: Final volume will be 1010 mL after glutamine addition.

Since glutamine degrades relatively rapidly, it may be preferable to add immediately prior to using media. Expiration 2 weeks after glutamine is added; base media can be kept longer w/o glutamine.

| FN-lite Macro for SHAM 10× - Stock #1 (per liter) | |
|---|---|
| (NH$_4$)2SO$_4$ (ammonium sulfate) | 4.63 g |
| KNO$_3$ (potassium nitrate) | 28.3 g |
| MgSO$_4$*H$_2$0 (magnesium sulfate heptahydrate) | 3.7 g |
| KH$_2$PO$_4$ (potassium phosphate, monobasic) | 1.85 g |
| Bring to volume | |
| Autoclave | |

| MS Micro 1000× - Stock #2 (per 1 liter) | |
|---|---|
| H$_3$BO$_3$ (boric acid) | 6.2 g |
| MnSO$_4$*H$_2$O (manganese sulfate monohydrate) | 16.9 g |
| ZnSO4*7H20 (zinc sulfate heptahydrate) | 8.6 g |
| Na$_2$MoO$_4$*2H20 (sodium molybdate dihydrate) | 0.25 g |
| CuSO$_4$*5H$_2$0 (copper sulfate pentahydrate) | 0.025 g |
| CoCl$_2$*6H$_2$0 (cobalt chloride hexahydrate) | 0.025 g |
| KI (potassium iodide) | 0.8300 g |
| Bring to volume | |
| Autoclave | |

| FeEDTA 100× - Stock #3 (per liter) | |
|---|---|
| Na$_2$EDTA* (sodium EDTA) | 3.73 g |
| FeSO4*7H$_2$0 (iron sulfate heptahydrate) | 2.78 g |
| Bring to Volume | |
| Solution is photosensitive. Bottle(s) should be wrapped in foil to omit light. | |
| Autoclave | |

*EDTA must be completely dissolved before adding iron.

| Ca 100× - Stock #4 (per liter) | |
| --- | --- |
| CaCl$_2$*2H$_2$0 (calcium chloride dihydrate) | 44 g |
| Bring to Volume | |
| Autoclave | |

| B5 Vitamin 1000× - Stock #5 (per liter) | |
| --- | --- |
| Thiamine*HCl | 10 g |
| Nicotinic Acid | 1 g |
| Pyridoxine*HCl | 1 g |
| Myo-Inositol | 100 g |
| Bring to Volume | |
| Store frozen | |

| 4% Glutamine - Stock #6 (per liter) | |
| --- | --- |
| DDI water heated to 30° C. | 900 mL |
| L-Glutamine | 40 g |
| Gradually add while stirring and applying low heat. | |
| Do not exceed 35° C. | |
| Bring to Volume | |
| Filter Sterilize | |
| Store frozen* | |

*Note: Warm thawed stock in 31° C. bath to fully dissolve crystals.

Chlorsulfuron Stock

1 mg/mL in 0.01 N Ammonium Hydroxide

What is claimed is:

1. A recombinant DNA construct comprising:
   (a) a nucleotide sequence encoding a methyltransferase polypeptide having an amino acid sequence of at least 95% sequence identity to SEQ ID NO:4; or
   (b) a nucleotide sequence encoding a glucosyltransferase having the amino acid sequence of SEQ ID NO:6; or
   (c) a nucleotide sequence comprising the full complement of (a) or (b),
   wherein said nucleotide sequence is operably linked to at least one regulatory sequence, wherein said nucleotide sequence and said regulatory sequence are an artificial combination of two otherwise separated segments of sequence.

2. The recombinant DNA construct of claim 1, wherein the methyltransferase polypeptide comprises SEQ ID NO: 4, and the glucosyltransferase polypeptide comprises SEQ ID NO: 6.

3. The recombinant DNA construct of claim 1, wherein the nucleotide sequence encoding a methyltransferase comprises one of SEQ ID NOs:3 or 8, and the nucleotide sequence encoding a glucosyltransferase comprises one of SEQ ID NOs: 5 or 9.

4. A vector comprising the recombinant DNA construct of claim 1.

5. A method for transforming a cell, comprising transforming a cell with the recombinant DNA construct of claim 1.

6. A transformed cell comprising the recombinant DNA construct of claim 1.

7. A method for producing a transgenic plant comprising transforming a plant cell with the recombinant DNA construct of claim 1 and regenerating a transgenic plant from the transformed plant cell.

8. A transgenic plant comprising the recombinant DNA construct of claim 1.

9. A seed comprising the recombinant DNA construct of claim 1.

10. A transgenic plant comprising a recombinant DNA construct of claim 1 wherein said regulatory sequence is a heterologous promoter, said plant having an altered level of a triterpene when compared to a plant having wild type level of triterpene.

11. The plant of claim 10 wherein said triterpene is a saponin derived from β-amyrin and said level is increased.

12. The plant of claim 10 wherein said triterpene is a saponin derived from β-amyrin and said level is decreased.

13. The plant of claim 10, wherein said plant is selected from the group consisting of a monocot and a dicot.

14. The plant of claim 13, wherein said plant is selected from the group consisting of wheat, oat, rice, and corn.

15. A method of producing a plant resistant to at least one fungus comprising:
(a) transforming a plant cell with at least one recombinant DNA construct of claim 1 encoding a first enzyme of the triterpene pathway;
(b) growing the transformed plant cell from step (a) under conditions that promote the regeneration of a transgenic plant; and
(c) evaluating the transgenic plant of step (b) for increased resistance to at least one fungus when compared to a plant of the same species that is not transformed with said recombinant DNA construct.

16. A method of producing a plant with altered levels of methyltransferase, or glucosyltransferase comprising:
(a) transforming a plant cell with at least one recombinant DNA construct of claim 1;
(b) growing the transformed plant cell from step (a) under conditions that promote the regeneration of a transgenic plant; and
(c) evaluating the transgenic plant of step (b) for an altered level of methyltransferase, or glucosyltransferase when compared to the amount of methyltransferase, or glucosyltransferase in a plant of the same species that is not transformed with said recombinant DNA construct.

17. A method for producing a plant with an altered level of triterpene saponin comprising:
(a) transforming a plant cell with the recombinant DNA construct of claim 1;
(b) growing the transformed plant cell from step (a) under conditions that promote the regeneration of a transgenic plant; and
(c) evaluating the transgenic plant of step (b) for an altered level of triterpene saponin when compared to the amount of triterpene saponin in a plant of the same species that is not transformed with said recombinant DNA construct.

18. The method of claim 17 wherein said recombinant DNA construct further comprises at least a second polynucleotide of the triterpene pathway that regulates expression of a polypeptide encoded by said polynucleotide.

19. The method of claim 17 wherein said recombinant DNA construct further comprises at least a portion of at least one polynucleotide encoding an enzyme selected from the group consisting of β-amyrin synthase and CYP51H10.

* * * * *